(12) United States Patent
Peri

(10) Patent No.: US 9,988,428 B2
(45) Date of Patent: Jun. 5, 2018

(54) PEGYLATED BIOACTIVE PEPTIDES AND USES THEREOF

(71) Applicant: GRIFFON PHARMACEUTICALS INC., Montreal (CA)

(72) Inventor: Krishna G. Peri, Montreal (CA)

(73) Assignee: GRIFFON PHARMACEUTICALS INC., Montreal, QC ( * ) Notice: Subject to any disclaimer, the term of this patent is extended or adjusted under 35 U.S.C. 154(b) by 0 days. days.

(21) Appl. No.: 15/490,618

(22) Filed: Apr. 18, 2017

(65) Prior Publication Data

US 2017/0296628 A1 Oct. 19, 2017

Related U.S. Application Data

(60) Provisional application No. 62/324,600, filed on Apr. 19, 2016.

(51) Int. Cl.
*A61K 38/25* (2006.01)
*C07K 14/60* (2006.01)
*A61K 47/48* (2006.01)

(52) U.S. Cl.
CPC .............. *C07K 14/60* (2013.01); *A61K 38/25* (2013.01); *A61K 47/48215* (2013.01)

(58) Field of Classification Search
CPC ... A61K 38/25; A61K 47/48215; C07K 14/60
See application file for complete search history.

(56) References Cited

U.S. PATENT DOCUMENTS

| | | | |
|---|---|---|---|
| 4,622,312 A | 11/1986 | Felix et al. |
| 4,659,693 A | 4/1987 | Nestor et al. |
| 4,689,318 A | 8/1987 | Kaiser et al. |
| 4,914,189 A | 4/1990 | Schally et al. |
| 5,023,322 A | 6/1991 | Kovacs et al. |
| 5,084,442 A | 1/1992 | Felix et al. |
| 5,091,365 A | 2/1992 | Sandow et al. |
| 5,137,872 A | 8/1992 | Seely et al. |
| 5,696,089 A | 12/1997 | Felix et al. |
| 5,792,747 A | 8/1998 | Schally et al. |
| 5,846,936 A | 12/1998 | Felix et al. |
| 5,847,066 A | 12/1998 | Coy et al. |
| 5,854,216 A | 12/1998 | Gaudreau et al. |
| 5,861,379 A | 1/1999 | Ibea et al. |
| 6,551,996 B1 | 4/2003 | Schwartz et al. |
| 7,144,577 B2 | 12/2006 | Torres et al. |
| 7,256,258 B2 | 8/2007 | Piquet et al. |
| 7,316,997 B2 | 1/2008 | Abribat et al. |
| 8,361,964 B2 | 1/2013 | Peri et al. |
| 8,435,945 B2 | 5/2013 | Abribat et al. |
| 8,481,489 B2 | 7/2013 | Abribat et al. |
| 8,796,216 B2 | 8/2014 | Johnstone et al. |
| 9,096,684 B2 | 8/2015 | Kawahata et al. |
| 2003/0148948 A1 | 8/2003 | Schwartz et al. |
| 2005/0059605 A1 | 3/2005 | Peri et al. |
| 2006/0128615 A1 | 6/2006 | Gaudreau et al. |
| 2009/0023646 A1 | 1/2009 | Gaudreau et al. |
| 2010/0331246 A1* | 12/2010 | Dimarchi ............ A61K 9/0019 514/5.9 |
| 2011/0021429 A1 | 1/2011 | Gaudreau et al. |
| 2011/0288011 A1 | 11/2011 | Castaigne et al. |
| 2014/0058068 A1 | 2/2014 | Schally et al. |
| 2014/0219983 A1 | 8/2014 | Madec et al. |
| 2017/0037105 A1* | 2/2017 | Samant .................. C07K 14/60 |

FOREIGN PATENT DOCUMENTS

| WO | 99/27897 | 6/1999 |
|---|---|---|
| WO | 2007/104567 | 9/2007 |

OTHER PUBLICATIONS

D'Antonio et al., Pharmacodynamic evaluation of a PEGylated analogue of human growth hormone releasing factor in rats and pigs. Growth Hormone & IGF Research, 14: 226-234 (2004).
Roberts et al., Chemistry for peptide and protein PEGylation. Advanced Drug Delivery Reviews, 54: 459-476 (2002).
Jevsevar et al., PEGylation of therapeutic proteins. Biotechnol. J., 5: 113-128 (2010).
International Search Report dated Jun. 15, 2017 for PCT/CA2017/050475, filed Apr. 18, 2017.
Written Opinion dated Jun. 15, 2017 for PCT/CA2017/050475, filed Apr. 18, 2017.
Felix, A.M. et al., Int. J. Pept. Res. 46(3-4):253-264 (1995).
Esposito, P. et al., Advanced Deug Deliv. Reviews 55: 1279-1291 (2003).
Campbell, R.M. et al., J. Pept. Res. 49(6):527-537 (1997).
Youn, S. Y. et al., Bioconj. Chem. 18:500-506 (2007).
Digilio, G. et al., J. Am. Chem. Soc. 125:3458-3470 (2003).
Pathier, Christoph et al., Trends in Biochemical Sciences 34(6): 303-310 (2009).
Kirkpatrick, Andrea at el., PNAS 109(49):19988-19993 (2012).
Lu, Yi-An et al., Reactive Polymers 22:221-229 (1994).
Lu, Yi-An et al.,Int. J. Peptide Protein Res. 43: 127-138 (1994).
Munafo, A. et al., Eur. J. Endocrinology 153:249-256 (2005).

* cited by examiner

*Primary Examiner* — Marcela M Cordero Garcia
(74) *Attorney, Agent, or Firm* — BCF LLP

(57) ABSTRACT

Described herein are bioactive peptides that are modified at one or more positions with a PEG moiety. An example of such a PEGylated bioactive peptide is a GHRH analog that is modified at one or more positions with a PEG moiety. Also described are pharmaceutically acceptable salts thereof and pharmaceutical compositions comprising such analogs or salts thereof, as well as methods, kits and uses thereof, for example for inducing or stimulating growth hormone secretion in a subject and for diagnosing, preventing or treating GH-deficient conditions in a subject.

20 Claims, 2 Drawing Sheets

PEGYLATED BIOACTIVE PEPTIDES AND USES THEREOF

CROSS REFERENCE TO RELATED APPLICATIONS

This application claims the benefit of U.S. provisional application No. 62/324,600, filed on Apr. 19, 2016, which is incorporated herein by reference in its entirety.

FIELD

The present disclosure relates to bioactive peptides conjugated to polyethylene glycol and uses thereof.

REFERENCE TO SEQUENCE LISTING

Pursuant to 37 C.F.R. 1.821(c), a sequence listing is submitted herewith as an ASCII compliant text file named "Sequence_Listing.txt" that was created on Apr. 18, 2017, and having a size of approximately 26,000 bytes. The content of the aforementioned file named "Sequence_Listing.txt" is hereby incorporated by reference in its entirety.

BACKGROUND

Growth hormone releasing hormone (GHRH), also known as growth hormone releasing factor (GRF or GHRF), is a 44-amino acid peptide secreted from neurons innervating anterior pituitary and elicits growth hormone (GH; also known as somatotropin) secretion from somatotroph cells. The minimally bioactive conformation of the GHRH peptide was identified to be present in the first 29 amino acids of the full length peptide (Frohman et al., 1986a), though low potency biological activity can be detected in GHRH (1-21) (Ling et al 1984a); GHRH peptides shorter than 21 amino acids were found to be inactive. GH is a physiological anabolic agent that is involved in increasing linear growth, muscle, bone and cartilage mass, and reduction of fat mass. GH deficiency, or a decrease in GH secretion, is known to be associated with short stature in children, fat gain particularly in the deep abdominal depots and increased cardiovascular risk.

The therapeutic utility of GHRH is compromised by the proteolytic lability of the peptide; GHRH is rapidly inactivated by dipeptidyl peptidase IV (DPPIV) in vivo through a cleavage between Ala2-Asp3 (Frohman et al., 1986b) and other proteases at Arg11-Lys12 and Lys12-Val13 (Frohman et al 1989). Various approaches have been used in order to provide proteolytically stable analogues of GHRH, including amino acid substitutions, cyclization of amino acid side chains, and modification with synthetic polymers and fatty acids.

The present description refers to a number of documents, the contents of which are herein incorporated by reference in their entirety.

SUMMARY

The present disclosure relates to bioactive peptides conjugated to polyethylene glycol (PEG) and uses thereof, such as analogs of GHRH with one or more attached PEG moieties.

In an aspect, there is provided a growth hormone releasing hormone (GHRH) analog comprising a peptide having the sequence set forth in formula (I) (SEQ ID NO: 1):

(I)

X1-X2-Asp-Ala-Ile-Phe-Thr-X8-X9-Tyr-X11-X12-Val-Leu-X15-Gln-Leu-X18-Ala-X20-X21-X22-Leu-X24-X25-X26-X27-X28-X29-X30 wherein:
X1 is Tyr, His, N-methyl Tyr or Desamino Tyr,
X2 is Ala, D-Ala, Ser or alpha aminoisobutyric acid (Aib);
X8 is Asn, Asp, Ala, Gln, Ser or Aib;
X9 is Ser, Asp, Ala or Cys conjugated to a PEG polymer of less than or equal to about 5 kDa;
X11 is Arg or L-Homoarginine (Har);
X12 is Lys or L-Ornithine (Orn);
X15 is Gly or Ala;
X18 is Ser or Ala;
X20 is Arg or Har;
X21 is Lys or Orn;
X22 is Leu, Val, Ala or Cys conjugated to a PEG polymer of less than or equal to about 5 kDa;
X24 is Gln or Cys conjugated to a PEG polymer of less than or equal to about 5 kDa;
X25 is Asp or Ala;
X26 is Ile or Ala;
X27 is Met, Leu or Norleucine;
X28 is Ser, Ala or Cys conjugated to a PEG polymer of less than or equal to about 5 kDa;
X29 is Lys, Arg, Orn, Har, or Agmantine; and
X30 is an $NH_2$ group or Asn-$NH_2$;
wherein at least one of X9, X22, X24 and X28 is Cys conjugated to a PEG polymer of less than or equal to about 5 kDa;
or a pharmaceutically acceptable salt thereof.

In an embodiment, X9 is Cys conjugated to a PEG polymer of less than or equal to about 5 kDa. In another embodiment, X22 is Cys conjugated to a PEG polymer of less than or equal to about 5 kDa. In another embodiment, X24 is Cys conjugated to a PEG polymer of less than or equal to about 5 kDa. In yet another embodiment, X28 is Cys conjugated to a PEG polymer of less than or equal to about 5 kDa.

In an embodiment, X9 and X22 are each independently Cys conjugated to a PEG polymer of less than or equal to about 5 kDa. In another embodiment, X9 and X24 are each independently Cys conjugated to a PEG polymer of less than or equal to about 5 kDa. In yet another embodiment, X9 and X28 are each independently Cys conjugated to a PEG polymer of less than or equal to about 5 kDa.

In some embodiments, X1 is Tyr. In some embodiments, X2 is Ala or D-Ala. In an embodiment, X2 is D-Ala. In some embodiments, X8 is Ala. In some embodiments, X9 is Ser. In some embodiments, X11 is Arg or Har; in an embodiment, X11 is Arg. In some embodiments, X12 is Lys or Orn; in an embodiment, X12 is Orn. In some embodiments, X15 is Ala. In some embodiments, X18 is Ser. In some embodiments, X20 is Arg or Har; in an embodiment, X20 is Arg. In some embodiments, X21 is Lys or Orn; in an embodiment, X21 is Orn. In some embodiments, X22 is Ala. In some embodiments, X24 is Gln. In some embodiments, X25 is Asp. In some embodiments, X26 is Ile. In some embodiments, X27 is Leu. In some embodiments, X28 is Ser. In some embodiments, X29 is Lys, Orn or Har; in an embodiment, X29 is Lys; in another embodiment, X29 is Har. In some embodiments, X30 is Asn-$NH_2$.

In some embodiments of formula (I), the PEG polymer of less than or equal to about 5 kDa described herein is a PEG polymer of about 2 kDa.

In some embodiments, the GHRH analog provided herein comprises a peptide which is:

YaDAIFTAC(Peg-5K)YROVLAQLSAROALQDILSZ; (SEQ ID NO: 2)

YaDAIFTASYROVLAQLSAROC(Peg-5K)LQDILSZ; (SEQ ID NO: 3)

YaDAIFTASYROVLAQLSAROALC(Peg-5K)DILSZ; (SEQ ID NO: 4)

YaDAIFTASYROVLAQLSAROALQDILC(Peg-5K)Z; (SEQ ID NO: 5)

YaDAIFTAC(Peg-5K)YROVLAQLSAROC(Peg-5K)LQDILSZ; (SEQ ID NO: 6)

YaDAIFTAC(Peg-5K)YROVLAQLSAROALC(Peg-5K)DILSZ; or (SEQ ID NO: 7)

YaDAIFTAC(Peg-5K)YROVLAQLSAROALQDILC(Peg-5K)Z; (SEQ ID NO: 8)

wherein: a is D-Ala; 0 is L-Ornithine (Orn); C(Peg-5K) is Cys conjugated to a PEG polymer of less than or equal to about 5 kDa; and Z is Lys, Arg, Har or Agmantine; or a pharmaceutically acceptable salt thereof. In some embodiments, the GHRH analog comprises a peptide having the sequence set forth in any one of SEQ ID Nos: 2-8; in some embodiments, such analogs further comprise one or more additional amino acid linked to Z.

In some embodiments, the GHRH analog provided herein is:

YaDAIFTASYROVLAQLSAROALQDILC(Peg-2K)KN-NH₂; (SEQ ID NO: 9)

YaDAIFTASYROVLAQLSAROALC(Peg-2K)DILSKN-NH₂; (SEQ ID NO: 10)

YaDAIFTASYROVLAQLSAROC(Peg-2K)LQDILSKN-NH₂; (SEQ ID NO: 11)

YaDAIFTASYROVLAQLSC(Peg-2K)ROALQDILSKN-NH₂; (SEQ ID NO: 12)

YaDAIFTASYROVLC(Peg-2K)QLSAROALQDILSKN-NH₂; (SEQ ID NO: 13)

YaDAIFTAC(Peg-2K)YROVLAQLSAROALQDILSKN-NH₂; (SEQ ID NO: 14)

YaDAIFTC(Peg-2K)SYROVLAQLSAROALQDILSKN-NH₂; (SEQ ID NO: 15)

YaDAIFTASYROVLAQLSAROALQDC(Peg-2K)LSKN-NH₂; (SEQ ID NO: 16)

YaDAIFTASYROVLAC(Peg-2K)LSAROALQDILSKN-NH₂; (SEQ ID NO: 17)

YaDAIFTAC(Peg-2K)YROVLAQLSAROALQDILS-(Har)-NH₂; (SEQ ID NO: 18)

YaDAIFTAC(Peg-2K)YROVLAQLSAROALQDILSRNC(Peg-2K)-NH₂; (SEQ ID NO: 19)

YaDAIFTAC(Peg-2K)YROVLAQLSAROALQDILC(Peg-2K)RN-NH₂; (SEQ ID NO: 20)

YaDAIFTAC(Peg-2K)YROVLAQLSAROALC(Peg-2K)DILSRN-NH₂; (SEQ ID NO: 21)

YaDAIFTAC(Peg-2K)YROVLAQLSAROC(Peg-2K)LQDILSRN-NH₂; (SEQ ID NO: 22)

YaDAIFTAC(Peg-5K)YROVLAQLSAROALQDILS(Har)-NH₂; or (SEQ ID NO: 23)

YaDAIFTAC(Peg-40K)YROVLAQLSAROALQDILS(Har)-NH₂; (SEQ ID NO: 24)

wherein: a is D-Ala; O is L-Ornithine (Orn); C(Peg-2K) is Cys conjugated to a PEG polymer of about 2 kDa; C(Peg-5K) is Cys conjugated to a PEG polymer of less than or equal to about 5 kDa; C(Peg-40K) is Cys conjugated to a PEG polymer of about 40 kDa; and Har is L-Homoarginine; or a pharmaceutically acceptable salt thereof.

In some embodiments, the GHRH analog or salt thereof comprises a peptide having the sequence set forth in any one of SEQ ID NOs: 1-11, 14, and 18-24, as defined herein, or a pharmaceutically acceptable salt thereof.

In some embodiments, the GHRH analog or salt thereof consists of a peptide having the sequence set forth in any one of SEQ ID NOs: 1-11, 14, and 18-24, as defined herein, or a pharmaceutically acceptable salt thereof.

In some embodiments, the GHRH analog provided herein is any one of SEQ ID Nos: 9, 10, 11, 14, 18, 20, 21, and 22, or a pharmaceutically acceptable salt thereof.

In embodiments, the GHRH analog or salt thereof provided herein further comprises (i) an amino-terminal modifying group; (ii) a carboxy-terminal modifying group; or (iii) both (i) and (ii). In an embodiment, the carboxy-terminal modifying group is NH₂.

In a further aspect, there is provided a pharmaceutical composition comprising a GHRH analog or salt thereof provided herein. In an embodiment, the pharmaceutical composition further comprises one or more pharmaceutically acceptable carriers, excipients, and/or diluents.

In a further aspect, there is provided a method for inducing growth hormone secretion in a subject in need thereof, comprising administering to the subject an effective amount of a GHRH analog or salt thereof described herein, or a pharmaceutical composition described herein.

In a further aspect, there is provided a method for increasing the level of growth hormone in a subject in need thereof, comprising administering to the subject an effective amount of a GHRH analog or salt thereof described herein, or a pharmaceutical composition described herein.

In a further aspect, there is provided a use of a GHRH analog or salt thereof described herein, or a pharmaceutical composition described herein, for inducing growth hormone secretion in a subject.

In a further aspect, there is provided a use of a GHRH analog or salt thereof described herein, or a pharmaceutical composition described herein, for increasing the level of growth hormone in a subject.

In a further aspect, there is provided a use of a GHRH analog or salt thereof described herein, or a pharmaceutical composition described herein, for the preparation of a medicament for inducing growth hormone secretion or increasing the level of growth hormone in a subject.

In a further aspect, there is provided a GHRH analog or salt thereof described herein, or a pharmaceutical composition described herein, for use in inducing growth hormone secretion or increasing the level of growth hormone in a subject.

In a further aspect, there is provided a GHRH analog or salt thereof described herein, or a pharmaceutical composition described herein, for the preparation of a medicament for inducing growth hormone secretion or increasing the level of growth hormone in a subject.

In a further aspect, there is provided a method for treating, preventing, or diagnosing a GH-deficient condition in a subject in need thereof, comprising administering to the subject an effective amount of a GHRH analog or salt thereof described herein, or a pharmaceutical composition described herein. Non-limiting examples of GH-deficient conditions that may be treated, prevented and/or diagnosed using methods provided herein include: HIV-associated lipohypertophy; HIV-associated dysmorphia/dysmetabolic syndrome (HADDS); growth hormone deficiency; Hypothalamic GH-RH deficiency; constitutional growth delay; pituitary dwarfism; growth retardation; wound or bone healing; osteoporosis; Turner Syndrome; Familial short stature; chronic renal insufficiency and severe growth retardation; intrauterine growth retardation; GH deficiency following radiotherapy for pituitary or hypothalamic lesions; long-term treatment with glucocorticoids associated with subnormal rate of growth; and abdominal obesity associated with metabolic syndrome or HIV-associated lipohypertrophy.

In an embodiment, there is provided a method for diagnosing a growth hormone deficiency in a subject in need thereof, comprising administering to the subject an effective amount of a GHRH analog or salt thereof described herein, or a pharmaceutical composition described herein, and measuring the growth hormone response.

In an embodiment, there is provided a method for treating HIV-related lipodystrophy in a subject in need thereof, comprising administering to the subject an effective amount of a GHRH analog or salt thereof described herein, or a pharmaceutical composition described herein. In embodiments, the treating comprises treating visceral fat accumulation. In embodiments, the subject is receiving antiviral therapy.

In an embodiment, there is provided a method for treating pituitary dwarfism or growth retardation in a subject in need thereof, comprising administering to the subject an effective amount of a GHRH analog or salt thereof described herein, or a pharmaceutical composition described herein.

In an embodiment, there is provided a method for the treatment of wound or bone healing in a subject in need thereof, comprising administering to the subject an effective amount of a GHRH analog or salt thereof described herein, or a pharmaceutical composition described herein.

In an embodiment, there is provided a method for the treatment of osteoporosis in a subject in need thereof, comprising administering to the subject an effective amount of a GHRH analog or salt thereof described herein, or a pharmaceutical composition described herein.

In an embodiment, there is provided a method for improving protein anabolism in a subject in need thereof, comprising administering to the subject an effective amount of a GHRH analog or salt thereof described herein, or a pharmaceutical composition described herein.

In an embodiment, there is provided a method for inducing a lipolytic effect in a subject in need thereof, comprising administering to the subject an effective amount of a GHRH analog or salt thereof described herein, or a pharmaceutical composition described herein. In embodiments, the subject is inflicted with clinical obesity.

In an embodiment, there is provided a method for the treatment of HIV-associated dysmorphia/dysmetabolic syndrome (HADDS) in a subject in need thereof, comprising administering to the subject an effective amount of a GHRH analog or salt thereof described herein, or a pharmaceutical composition described herein.

In embodiments of the methods and uses provided herein, an effective amount of the GHRH analog or salt thereof described herein, or the pharmaceutical composition described herein, is administered to the subject.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
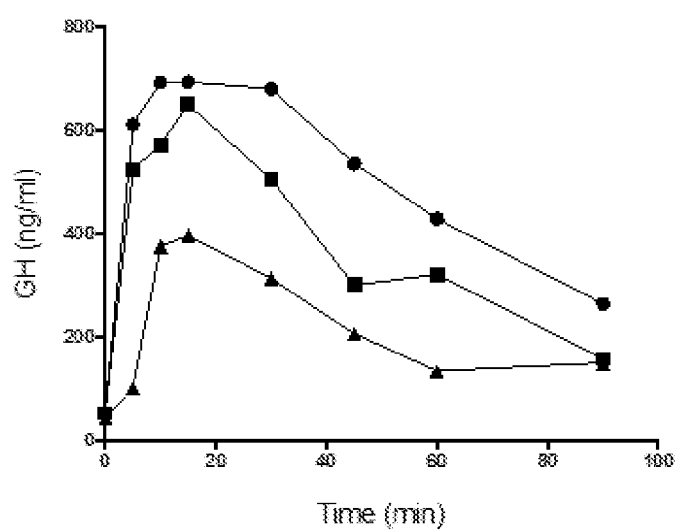
FIG. 1 is a graph showing stimulation of Growth Hormone secretion vs. time after administration by peptides containing PEG2K chains at the $8^{th}$ position (Analog 7-Triangles), the $9^{th}$ position (Analog 6-squares) and the $28^{th}$ position (Analog 1-Circles).

GHRH (or GRF or GHRF) refers to growth hormone releasing peptide or growth hormone releasing hormone. This hypothalamic hormone is a 44 amino acid peptide and the bioactive fragment of GHRH is a 29 amino acid peptide, $GHRH_{1-29}$. The full length $GHRH_{1-44}$ and the bioactive fragment $GHRH_{1-29}$ thus differ in the sequence corresponding to positions 30-44 in $GHRH_{1-44}$.

Native human GHRH (also referred to as $GHRH_{1-44}$) has the following structure:

(SEQ ID NO: 26)
YADAIFTNSYRKVLGQLSARKLLQDIMSRQQGESNQERGARARL-amide.

$GHRH_{1-29}$ has the following structure:

(SEQ ID NO: 25)
YADAIFTNSYRKVLGQLSARKLLQDIMSR-amide.

The sequence corresponding to positions 30-44 of native human GHRH is:

(SEQ ID NO: 27)
QQGESNQERGARARL.

Intermediate forms between $GHRH_{1-29}$ and $GHRH_{1-44}$, e.g., $GHRH_{1-29}$ having added at its C-terminus one or more amino acids of the first 14 amino acids (in embodiments, the first 1, 2, 3, 4, 5, 6, 7, 8, 9, 10, 11, 12, 13 or 14 contiguous amino acids) of the sequence corresponding to positions 30-44 noted above (SEQ ID NO: 27), also have GHRH activity. All GHRH peptides comprising the bioactive 1-29 segment, or variants thereof as described herein, are subject to the improvements and modifications described herein.

Clinically useful therapeutics have been derived from both the full length peptide, e.g., N-hexenoyl-GHRH(1-44)-amide which has an N-hexenoyl modification at the N-terminus and is commercially known as tesamorelin or Egrifta®, and the 29 amino acid bioactive peptide GHRH (1-29)-amide, which is commercially known as Sermorelin or GEREF®, and have been prescribed for treatment of HIV-associated lipohypertophy and diagnosis of growth hormone deficiency, respectively. Various modifications of GHRH have been studied (see, e.g., Campbell et al., 1991, 1992, 1994 and 1997; Cervini et al., 1998; Ling et al., 1984a and 1984b; Kubiak et al., 1993; Sato et al., 1987 and 1990; Felix et al., 1988 and 1995; Hodate et al., 1986; Bokser et al., 1990; Zarandi, et al., 1990, 1992 and 1994; Kovacs et al., 1988; Murphy et al., 1988; Freidman et al. 1991; and US patents/published applications U.S. Pat. No. 4,914,189; US20090023646; US20060128615; U.S. Pat. No. 8,435,945; U.S. Pat. No. 8,481,489; U.S. Pat. No. 7,316,997; U.S. Pat. No. 8,361,964; U.S. Pat. No. 5,023,322; U.S. Pat. No. 4,689,318; U.S. Pat. No. 4,659,693; U.S. Pat. No. 6,551,996; U.S. Pat. No. 7,256,258; US20030148948; U.S. Pat. No. 5,084,442; U.S. Pat. No. 5,137,872; U.S. Pat. No. 5,846,936; U.S. Pat. No. 4,622,312; U.S. Pat. No. 5,696,089; US20050059605; U.S. Pat. No. 5,091,365; U.S. Pat. No. 5,847,066; U.S. Pat. No. 9,096,684; U.S. Pat. No. 5,792,747; US20140058068; and US20110288011). The GHRH peptides described in the above publications and patents are incorporated by reference herein.

Pegylation of GHRH peptide at certain positions has been studied. For example, PEGylation at the N-terminus (Tyr1), Lys12, Lys21 or at the C-terminus (using a GGC-linker) has been studied, and it was found that attachment of PEG chains at the internal positions, Lys12 and Lys21 decreased potency but increased biological half-life (Campbell et al., 1997; Felix et al. 1995; Youn et al. 2007; Lu et al. 1994; Digilio et al. 2003; Lu et al. 1993; Esposito et al. 2003). PEG chains (2K, 5K or 10K) at Asp8 or Lys12 decreased biological potency. Carboxyterminal Pegylation, regardless of molecular weight (MW), increased biological activity (Felix et al., 1995). It was reasonable to expect therefore that covalent modification with bulky PEG chains in the N-terminal half of the GHRH molecule would decrease its biological activity, owing to the fact almost all of the residues in the N-terminus make intimate contacts within the GHRH receptor. In view of the currently accepted view of ligand binding of GHRH receptor, it was surprising to find, as provided herein, that PEGylation at the $9^{th}$ amino acid, but not at the $8^{th}$ amino acid of GHRH, resulted in a biologically potent peptide.

In order to explore novel positions for PEGylation within the $GHRH_{1-29}$ peptide, the present inventor has developed novel GHRH analogs via covalent modification of GHRH at certain novel amino acid positions with a PEG moiety. Polyethylene glycol (PEG) refers to polymers of ethylene glycol which are commercially produced with different molecular weights (e.g., 200-50,000 kDa or more). Such modified analogs were prepared by substitution of certain amino acids in GHRH with an amino acid having a side chain group which can be modified with a suitable group-reactive reagent. For example, a Cys side chain may be modified with a thiol-reactive agent, or a Lys side chain may be modified with an amine-reactive agent. For example, substitution with one or more Cys residues, followed by reaction with a thiol-reactive maleimido-PEG, results in GHRH analogs having one or more Cys substitutions and covalently modified with PEG at the Cys side chains. As described herein, $GHRH_{1-29}$ (i.e., the truncated form of GHRH containing the first 29 amino acids and which retains biological activity) was used, and such substitution and PEG modification was studied at positions 8, 9, 15, 16, 19, 22, 24, 26, 28 and 30 (the latter case representing addition of an amino acid (e.g., Cys) at the C-terminus of $GHRH_{1-29}$, its side chain being modified by PEG, creating a 30 amino acid GHRH analog having a PEG-modified C-terminal residue). As described in the Examples herein, Cys-substituted peptides (at positions 8, 9, 15, 16, 19, 22, 24, 26, 28 and 30) were synthetically produced using solid phase peptide synthesis, purified and reacted with maleimido-PEG (2000 MW). The PEGylated peptides were purified, lyophilized and subjected to further analysis.

There are provided herein GHRH analogs that are PEG-modified GHRH or active fragments and/or variants thereof, e.g., GHRH or active fragments and/or variants thereof, comprising one or more covalently attached PEG moieties. These GHRH analogs exhibit agonistic activity on cells expressing the GHRH receptor (GHRHr), and induce GH secretion in animal models. The terms "GHRH" (growth hormone-releasing hormone) and "GRF" (growth hormone-releasing factor) are used interchangeably herein. Similarly, the terms "GHRH receptor", "GHRHr", "GRF receptor" and "GRFr", are used interchangeably herein.

In an aspect, there is provided a growth hormone releasing hormone (GHRH) analog comprising a Peptide having the sequence set forth in formula (I) (SEQ ID NO: 1):

(I)
X1-X2-Asp-Ala-Ile-Phe-Thr-X8-X9-Tyr-X11-X12-Val-
Leu-X15-Gln-Leu-X18-Ala-X20-X21-X22-Leu-X24-X25-
X26-X27-X28-X29-X30 wherein:
X1 is Tyr, His, N-methyl Tyr or Desamino Tyr,
X2 is Ala, D-Ala, Ser or alpha aminoisobutyric acid (Aib);
X8 is Asn, Asp, Ala, Gln, Ser or Aib;
X9 is Ser, Asp, Ala or Cys conjugated to a PEG polymer of less than or equal to about 5 kDa;
X11 is Arg or L-Homoarginine (Har);
X12 is Lys or L-Ornithine (Orn);
X15 is Gly or Ala;
X18 is Ser or Ala;
X20 is Arg or Har;
X21 is Lys or Orn;
X22 is Leu, Val, Ala or Cys conjugated to a PEG polymer of less than or equal to about 5 kDa;
X24 is Gln or Cys conjugated to a PEG polymer of less than or equal to about 5 kDa;
X25 is Asp or Ala;
X26 is Ile or Ala;
X27 is Met, Leu or Norleucine;
X28 is Ser, Ala or Cys conjugated to a PEG polymer of less than or equal to about 5 kDa;
X29 is Lys, Arg, Orn, Har, Agmantine; and
X30 is an $NH_2$ group or Asn-$NH_2$;
or a pharmaceutically acceptable salt thereof.

In an embodiment, at least one of X9, X22, X24 and X28 is Cys conjugated to a PEG polymer of less than or equal to about 5 kDa.

In embodiments, the GHRH analog may comprise, further to the peptide having the sequence set forth in formula (I) as defined herein, one or more amino acid (naturally occurring or synthetic) covalently linked to the carboxy-terminus of the peptide. In embodiments, the GHRH analog comprises up to 25 additional amino acids at the C-terminus of the peptide set forth in formula (I) as defined herein. In further embodiments, the GHRH analog comprises up to 20, 19, 18, 17, 16, 15, 14, 13, 12, 11, 10, 9, 8, 7, 6, 5, 4, 3, 2, or 1 additional amino acids at the C-terminus of the peptide set forth in formula (I) as defined herein. In embodiments, the GHRH analog contains about 60 residues or less, in further embodiments about 55, about 50, about 45, about 40 or about 35 residues or less. In embodiments, the GHRH analog contains between about 29 residues to about 60 residues. In further embodiments, the GHRH analog contains between about 29 residues to about 50 residues. In further embodiments, the GHRH analog contains between about 29 residues to about 44 residues.

In embodiments, the GHRH analog may further comprise an N-terminal group such as a $C_1$-$C_{16}$ acyl group (straight or branched, saturated or unsaturated); in a further embodiment, a $C_1$-$C_{10}$ acyl group (straight or branched, saturated or unsaturated); in a further embodiment, a saturated $C_1$-$C_6$ acyl group (straight or branched); or an unsaturated $C_3$-$C_6$ acyl group (straight or branched). In a further embodiment, the GHRH analog may further comprise an acetyl group ($CH_3$—CO—, Ac). In still further embodiments, the GHRH analog may further comprise ($C_1$-$C_6$) alkyl, ($C_2$-$C_6$) alkenyl, ($C_2$-$C_6$) alkynyl, substituted ($C_1$-$C_6$) alkyl, substituted ($C_2$-$C_6$) alkenyl, substituted ($C_2$-$C_6$) alkynyl, propyl, butyl pentyl, hexanoyl or hexenoyl.

In embodiments, the GHRH analog may further comprise a C-terminal group of the formula —$NH_2$, —NHR, or —NRR, wherein R is a $C_1$-$C_{16}$ acyl group (straight or branched, saturated or unsaturated); in a further embodiment, a $C_1$-$C_{10}$ acyl group (straight or branched, saturated or unsaturated); in a further embodiment, a saturated $C_1$-$C_6$ acyl group (straight or branched) or an unsaturated $C_3$-$C_6$ acyl group (straight or branched); in a further embodiment, an acetyl group ($CH_3$—CO, Ac); in further embodiments, ($C_1$-$C_6$) alkyl, ($C_2$-$C_6$) alkenyl, ($C_2$-$C_6$) alkynyl, substituted ($C_1$-$C_6$) alkyl, substituted ($C_2$-$C_6$) alkenyl, or substituted ($C_2$-$C_6$) alkynyl); or in further embodiments, the C-terminal group could be a straight or branched PEG chain of more than 2 kDa.

In embodiments, the GHRH analog or salt thereof comprises a peptide having the sequence set forth in any one of SEQ ID NOs: 1-11, 14, and 18-24, as defined herein.

Polyethylene Glycol (PEG) and PEGylation

"Polyethylene glycol" or "PEG" refers to polymers of ethylene glycol, in a branched or straight chain, represented by the general formula $HO(CH_2CH_2O)_nH$, where n is an integer of at least 2. PEG includes polymers of ethylene glycol with an average total molecular weight selected from the range of about 500 to about 50,000 Daltons or more. The average molecular weight of a PEG chain is indicated by a number, e.g., PEG-5,000 or Peg-5K refers to polyethylene glycol chain having a total molecular weight average of about 5,000 Daltons, or about 5 kiloDaltons or kDa or K (1 kDa=1K=1000 Daltons). Various sizes of PEG are commercially available and may be used in the products and methods described herein, e.g., having an average size of about 200, about 300, about 400, about 500, about 600, about 1,000, about 1,500, about 2,000, about 3,000, about 3,350, about 4,000, about 5,000, about 6,000, about 8,000, about 10,000, about 12,000, about 20,000, about 35,000 or about 50,000 Daltons.

In an embodiment, the one or more PEG moieties described herein have an average molecular weight of less than or equal to about 5 kDA (also referred to herein as 5K).

In further embodiments, the one or more PEG moieties described herein have an average molecular weight of from about 2 kDa to about 5 kDa, or of about 1, about 2, about 3, about 4 or about 5 kDa. In a further embodiment, the one or more PEG moieties described herein are about 2 kDa. Further, in embodiments, a GHRH analog described herein having multiple PEG modifications may be modified by PEG moieties of different sizes, i.e., the same analog may have attached thereto PEG moieties of different sizes. In a further embodiment, a GHRH analog described herein having multiple PEG modifications may be modified by PEG moieties of about the same size.

PEGylation (i.e., attachment of a PEG moiety) of the GHRH analogs described herein may be carried out by methods known in the art. For example, a reactive PEGylation reagent that is reactive to a specific amino acid side chain may be used. An example is a thiol- or sulfhydryl-reactive PEG, e.g., having a maleimide moiety (PEG-maleimide), which can react with the Cys side chain. A further example is an amine-reactive PEG, e.g., having an N-hydroxysuccinimide ester (PEG-NHS ester), which can react with an amine side chain (e.g., Lys). In embodiments, PEG modification may be at the N- and/or C-terminus, using reagents which are amine- or carboxy-reactive. In further embodiments, PEG modification may be through a linker, i.e., a linker or spacer moiety located between the PEG moiety and the peptide. Such linkers include, for example, heterobifunctional or homobifunctional reagents.

Amino Acids

"Amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Other amino acids include, for example, non-genetically encoded forms of amino acids, such as beta-alanine, 3-amino-propionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Har), N-acetyl lysine, 2-amino butyric acid, 2-amino butyric acid, 2,4,-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3-diaminobutyric acid (D- or L-), etc.

In embodiments, GHRH analogs described herein may include substitutions of functionally equivalent amino acid residues. For example, one or more amino acid residues within the sequence can be substituted by another amino acid having similar physico-chemical properties, i.e., of the same group or family with respect to one or more properties. Substitutions made within a family of amino acids are generally understood to be conservative substitutions, i.e., conservative substitutions may be defined as exchanges within one of the following five groups: (i) small, aliphatic, non-polar residues: Ala, Gly; (ii) large, non-polar residues: Met, Leu, Ile, Val, Pro; (iii) uncharged polar residues: Ser, Thr, Cys, Tyr, Gly; (iv) polar, negatively-charged residues: Asp, Glu, and their amides: Asn, Gln; (v) polar, positivelycharged residues: His, Arg, Lys; and (vi) large aromatic residues: Phe, Tyr, Trp. Other examples of amino acid substitutions are as follows: Tyr (N-methyl Tyr, Deamino-Tyr, His, D-tyr); Ala (D-Ala, Aib, Abu); Val/Leu/Ile (interchangeable in certain positions); Asn (Gin); Met (Norleucine, Leu); Lys (Homolysine, Arginine, Homoarginine (Har), ornithine, Gamma aminobutyric acid (Gab), Gamma aminopropionic acid (Gap), Agmantine); Arg (homoarginine, lysine, homolysine, ornithine, Gamma aminobutyric acid (Gab), Gamma aminopropionic acid (Gap), Agmantine); Asp/Glu (interchangeable in certain positions); and Ser/Thr (interchangeable in certain positions).

GHRH analogs described herein may comprise all L-amino acids or a mixture of L- and D-amino acids. In an embodiment, the GHRH analog provided herein comprises at least one D-amino acid, such as in one embodiment, D-Ala. In an embodiment, said at least one D-amino acid is located in the N-terminal portion of the GHRH analog provided herein (e.g., within the last 2 or 3 N-terminal residues). The presence of one or more D-amino acids typically results in peptides which have increased stability (e.g., in vivo) due to decreased susceptibility to protease/peptidase cleavage, but which retain biological activity.

Peptide Synthesis

Peptides can be readily synthesized by manual and automated solid phase procedures well known in the art. Suitable syntheses can be performed for example by utilizing "T-boc" or "Fmoc" procedures. Techniques and procedures for solid phase synthesis are described in, for example, Solid Phase Peptide Synthesis: A Practical Approach, by E. Atherton and R. C. Sheppard, published by IRL, Oxford University Press, 1989. Alternatively, the peptides may be prepared by way of segment condensation, as described, for example, in Liu et al., 1996; Baca et al., 1995; Tam et al., 1995; Schnolzer and Kent, 1992; Liu and Tam, 1994a; Liu and Tam, 1994b; and Yamashiro and Li, 1988. Other methods useful for synthesizing the peptides are described in Nakagawa et al., 1985.

Peptides and peptide analogs comprising naturally occurring amino acids encoded by the genetic code may also be prepared using recombinant DNA technology using standard methods. Peptides produced by recombinant technology may be modified (e.g., by N-terminal acylation, by acetylation, by C-terminal amidation, etc.), using methods well known in the art.

Therefore, in embodiments, in cases where a GHRH analog described herein contains naturally occurring amino acids encoded by the genetic code, the GHRH analog may be produced using recombinant methods, and may in embodiments be subjected to, for example, the modifications noted above (e.g., acylation, amidation, etc.). Accordingly, in another aspect, there is provided a nucleic acid encoding a GHRH analog provided herein. In another aspect, there is provided a recombinant vector comprising the nucleic acid; in a further aspect, there is provided a host cell comprising the recombinant vector.

GHRH analogs described herein can be purified by many techniques of peptide purification well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art. For affinity chromatography purification, any antibody which specifically binds the peptide or peptide analog may, for example, be used.

Pharmaceutically Acceptable Salts

GHRH analogs described herein are basic but contain both negative and positive charges; therefore, salts can be formed using both cations as well as anions. GHRH analogs described herein may thus be in the form of a salt, e.g., pharmaceutically acceptable, nontoxic salts, such as acid addition salts. "Pharmaceutically acceptable salt" refers to salts of compounds that retain the biological activity of the parent compound and which are not biologically or otherwise undesirable. Such salts can be prepared in situ during the final isolation and purification of a GHRH analog, or may be prepared separately by reacting a free base function with a suitable acid. Many of the GHRH analogs disclosed herein are capable of forming acid and/or base salts by virtue of the presence of amino and/or carboxyl groups or groups similar thereto. Examples of pharmaceutically acceptable acid addition salts include, but are not limited to, hydrochloride, hydrobromide, sulphate, phosphate, fumarate, gluconate, tannate, maleate, acetate, trifluoroacetate, citrate, benzoate, succinate, alginate, pamoate, malate, ascorbate, tartarate, and the like. Particularly preferred are salts of low solubility, e.g., low molecular fatty acids ($C_4$-$C_{12}$), pamoate and the like. Other salts include metal cations such as $Zn^{+2}$ and $Mg^{+2}$, which may exhibit long duration of activity.

Compositions/Formulations

In another aspect, there is provided a composition (e.g., a pharmaceutical composition) or formulation comprising a GHRH analog or salt thereof described herein. In an embodiment, the composition further comprises one or more pharmaceutically acceptable carriers, excipient, and/or diluents.

As used herein, "pharmaceutically acceptable" (or "biologically acceptable") refers to materials which have (little or) no toxic or adverse biological effects in vivo. It refers to those compounds, compositions, and/or dosage forms which are suitable for use in contact with biological fluids and/or tissues and/or organs of a subject (e.g., animal, mammal, human) without excessive toxicity, irritation, allergic response, or other problem or complication, commensurate with a reasonable benefit/risk ratio.

The term "pharmaceutically acceptable carriers, excipient, and/or diluents" refers to additives commonly used in the preparation of pharmaceutical compositions and includes, for example, solvents, dispersion media, saline solutions, surfactants, solubilizing agents, lubricants, emulsifiers, coatings, antibacterial and antifungal agents, chelating agents, pH-modifiers, soothing agents, buffers, reducing agents, antioxidants, isotonic agents, absorption delaying agents or the like (see, e.g., Rowe et al., *Handbook of Pharmaceutical Excipients*, Pharmaceutical Press; 6$^{th}$ edition, 2009).

GHRH analogs described herein can also be formulated with anionic or neutral lipids to form peptide liposomes. For example, vasoactive intestinal peptide (VIP) was formulated with anionic phospholipids to prevent proteolytic degradation and to enhance biological activity in vivo (Gololobov, et al. 1998). In addition, PCT Publication WO 95/27496 and Gao, et al., 1994 describe the use of liposomes for delivery of VIP in comparison to its delivery in aqueous solution. Encapsulation of VIP in liposomes was found to protect the peptide from proteolytic degradation and to significantly enhance the ability of VIP and to effect a decrease in mean arterial pressure in comparison to VIP in aqueous solution in hypertensive hamsters. Liposomes may be produced from combinations of lipid materials well known and routinely utilized in the art to produce liposomes and including at least one lipid component covalently bonded to a water-soluble polymer. Lipids may include relatively rigid varieties, such as sphingomyelin, or fluid types, such as phospholipids having unsaturated acyl chains.

Polymers described herein may include any compounds known and routinely utilized in the art of SSL technology and technologies which are useful for increasing circulatory half-life for proteins, including for example polyvinyl alcohol, polylactic acid, polyglycolic acid, polyvinylpyrrolidone, polyacrylamide, polyglycerol, polyaxozlines, or synthetic lipids with polymeric headgroups. In embodiments, the polymer is PEG having an average molecular weight between about 1000 and about 5000 Daltons.

Lipids for producing liposomes described herein may include distearoyl-phosphatidylethanolamine covalently bonded to PEG (PEG-DSPE), phosphatidylcholine (PC), and/or phosphatidylglycerol (PG), in further combination with cholesterol (Choi). In one embodiment, a combination of lipids and cholesterol for producing liposomes comprises a PEG-DSPE:PC:PG:Chol molar ratio of 0.5:5:1:3.5.

Controlled release of GHRH analogs described herein can also be obtained through admixing high molecular weight polymers and suitable vehicles. Such techniques are well known in the art of controlled release of peptides and small molecules from injectable depot formulations. Polymers that are useful in conjunction with the methods and compositions provided herein are bioerodible, i.e., they gradually degrade, e.g., enzymatically, or hydrolyze, dissolve, physically erode, or otherwise disintegrate within the aqueous fluids of a patient's body. Generally, the polymers bioerode as a result of hydrolysis or physical erosion, although the primary bioerosion process is typically hydrolysis or enzymatic degradation.

Such polymers include, but are not limited to polylactides, polyglycolides, caprolactone-based polymers, polycaprolactones, polyanhydrides, polyamines, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, hydroxymethylcellulose polyphosphoesters, polyesters, polybutylene terephthalate, polysaccharides, chitin, chitosan, hyaluronic acid and copolymers, terpolymers and mixtures thereof. Examples of polymers as given in U.S. Pat. No. 7,368,126 B2, include, but are not limited to, Poly (D,L-lactide-co-glycolide) 50:50 RESOMER® RG502, Poly (D,L-lactide-co-glycolide) 50:50 RESOMER® RG502H, Poly D,L Lactide (RESOMER® R 202, RESOMER® R 203); Poly dioxanone (RESOMER® X 210) (Boehringer Ingelheim Chemicals, Inc., Petersburg, Va.). Additional examples include, but are not limited to, DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinnati, Ohio); Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone; Poly DL-lactide-co-caprolactone 25:75; and Poly DL-lactide-co-caprolactone 75:25 (Birmingham Polymers, Inc., Birmingham, Ala.).

Route of Administration

GHRH analogs or salts thereof and compositions thereof described herein may be administered to subjects (e.g., animals, mammals, humans) subcutaneously (s.c), intramuscularly (i.m.), intravenously (i.v), orally, or topically; intranasally or by pulmonary inhalation; by transdermal delivery; or in a depot form (e.g., microcapsules, microgranules, or cylindrical rod like implants) formulated from a biodegradable suitable polymer (such as D,L-lactide-coglycolide). In an embodiment, the microcapsules or microgranules are used as the depot form. Other equivalent modes of administration are also within the scope of the methods and compositions provided herein, i.e., continuous drip, cutaneous patches, depot injections, infusion pump and time release modes such as microcapsules and the like. Administration may be in any physiologically acceptable injectable carrier, physiological saline being acceptable, though other carriers known to the art may also be used.

GHRH analogs or salts thereof and compositions thereof are preferably administered parenterally, intramuscularly, subcutaneously or intravenously with a pharmaceutically acceptable carrier such as isotonic saline. Alternatively, GHRH analogs or salts thereof and compositions thereof may be administered as an intranasal spray with an appropriate carrier or by pulmonary inhalation. In one embodiment, a suitable route of administration is a depot form formulated from a biodegradable suitable polymer, e.g., poly-D,L-lactide-coglycolide, as microcapsules, microgranules or cylindrical implants containing dispersed antagonistic compounds.

Indications

GHRH elicits pulsatile growth hormone (GH) secretion from the pituitary. Therefore, GHRH analogs or salts thereof described herein may be useful for inducing or stimulating the secretion of GH in a subject. In an aspect, there is provided a method for inducing or stimulating the secretion of GH in a subject (in need thereof), comprising administering to the subject an effective amount of a GHRH analog or salt thereof, or a pharmaceutical composition comprising same, as described herein. Also provided is a use of a GHRH analog or salt thereof, or a pharmaceutical composition comprising same, described herein, for inducing or stimulating the secretion of GH in a subject. Also provided is a use of a GHRH analog or salt thereof, or a pharmaceutical composition comprising same, described herein, for the preparation of a medicament for inducing or stimulating the secretion of GH in a subject. Also provided is a GHRH analog or salt thereof, or a pharmaceutical composition comprising same, described herein, for use in inducing or stimulating the secretion of GH in a subject.

"Inducing" or "stimulating" as used herein refers to a measurable increase of a biological activity. In embodiments, the increase is at least about a 10%, 20%, 40%, 60%, 80%, 90%, 95%, 100% (2-fold), or 200% (3-fold) increase in the biological activity relative to a control. For example, a GHRH analog is found to stimulate GHRHr activity when an increase in GH levels is measured following administration of the GHRH analog or salt thereof to a subject (e.g., animal, human) in comparison to levels in the subject prior to administration, or relative to a control subject to whom the GHRH analog or salt thereof has not been administered.

GH action on the liver can lead to production of IGF-1 and its major binding protein, IGFBP3. Together these bioactive proteins can produce anabolic actions on muscle, bone and chondrocytes. GH can also stimulate lipolysis particularly from visceral adipose deposits. GHRH can also have direct and indirect actions on cardiac function, protection from ischemic sequelae, neurological enhancement resulting in elevated cognition, promotion of slow wave sleep and daytime vigilance. Lack of one or more of GH and GHRH can lead to GH and IGF-1 related pathologies. Therefore, GHRH analogs and salts thereof provided herein can be used to diagnose, as well as to treat or prevent, GH-deficient conditions. These conditions may include but are not limited to: (1) screening for growth hormone deficiency; (2) treatment of Hypothalamic GH-RH deficiency; (3) constitutional growth delay; (4) Turner Syndrome; (5) Familial short stature; (6) Prepubertal children with chronic renal insufficiency and severe growth retardation; (7) infants and children with intrauterine growth retardation; (8) children with GH deficiency following radiotherapy for pituitary or hypothalamic lesions; (9) children on long-term treatment with glucocorticoids and growing at subnormal rate; and other conditions mentioned hereinabove.

Further Clinical Applications of GHRH analogs in Adults may include, without limitation: To reduce or prevent the loss of muscle, bone and skin mass and lessen the increase of body fat that normally accompanies (1) the aging process; (2) catabolic states; (3) wound healing; (4) delayed healing of fractures; (5) osteoporosis; (6) abdominal Obesity which is a result of metabolic syndrome or HIV-associated lipohypertrophy; (7) as an adjunct to total parenteral nutrition in malnourished patients with chronic obstructive pulmonary disease; (8) cardiac failure; and (9) use during and after space flights to counteract the decrease in GH secretion. Weightlessness of space flight significantly decreases the release of growth hormone, which could explain the bone loss and muscle weakness many astronauts experience after prolonged space flights; (10) mild cognitive impairment (MCI) that is a part of the normal aging process or prequel to Alzheimer's disease or senile dementia or due to traumatic brain injury suffered in e.g., sports, accidental falls, or automobile accidents.

Diseases and conditions in which administration of GHRH analogs and salts thereof may be beneficial have been extensively described in the art (see, e.g., WO 2009/009727, WO 2006/042408, WO 2005/037307, and WO 2004/105789). Such conditions/disorders/diseases include, for example, syndromes associated with fat accumulation, hypercholesterolemia, obesity, syndrome X, lipohypertrophy, lipoatrophy, lipodystrophy (e.g., HIV-associated lipodystrophy syndrome), impaired cognitive function, impaired daytime vigilance, declined function of the immune system (e.g., immunodeficiencies such as T-cell deficiencies), muscle protein catabolism, diseases/conditions associated with muscle wasting such as sarcopenia, frailty, radiotherapy- and/or chemotherapy-related side effects (e.g., in HIV-infected and cancer patients), cachexia (e.g., in cancer patients), hypothalamic pituitary dwarfism, burns, osteoporosis, renal failure, non-union bone fracture, acute/chronic debilitating illness or infection, wound healing, post-surgical problems, lactation failure, infertility in women, neurodegenerative conditions, GHRH receptor-dependent tumors, and conditions related to aging or sleep disorders/impairment.

Therefore, in other aspects, there is provided a method for (1) stimulating daytime vigilance and/or cognitive function, e.g. in conditions related to aging, mild cognitive impairment (MCI), pre-Alzheimer's symptoms (Pre-Onset Alzheimer's), dementia and/or sleep impairment (e.g., age-related sleep impairment), (2) improving/preventing/treating metabolic conditions associated with fat accumulation and/or hypercholesterolemia (obesity, abdominal obesity/adiposity, abdominal obesity with metabolic disorders, abdominal obesity with relative GH deficiency, metabolic syndrome or syndrome X, lipohypertrophy, lipoatrophy, lipodystrophy (e.g., HIV-associated lipodystrophy syndrome), dyslipidemia, hypertriglyceridemia), (3) improving anabolism in catabolic/wasting conditions, such as those observed in acute or chronic renal failure (e.g., acute or chronic renal failure wasting), chronic heart failure (e.g., chronic heart failure wasting), chronic obstructive pulmonary disease (COPD), cystic fibrosis (e.g., cystic fibrosis wasting in adults), frailty, burns, infections (sepsis), muscular dystrophy, congestive heart failure, neurodegenerative conditions (Alzheimer's, pre-Alzheimer's syndromes, amyotrophic lateral sclerosis (ALS), AIDS, protein malnutrition following long-term corticosteroid therapy, following non-union bone fracture, hip fracture, trauma, or major surgery (post-surgical problems), osteoporosis, long-term immobilization, cancer-related cachexia, sarcopenia (e.g., age-related sarcopenia), GI malabsorption (Short Bowel Syndrome (SBS), Crohn's disease) particularly in elderly subjects, for example to increase muscle mass and/or function, (4) improving immune function or reconstitution of immunodeficient states (e.g., T-cell immunodeficiencies) such as that associated aging, HIV infection/AIDS or following high-dose chemotherapy and/or radiotherapy (in HIV-infected and cancer patients), (5) altering a lipid parameter ((a) decreasing cholesterol; (b) decreasing non-HDL cholesterol; (c) decreasing triglycerides; and/or (d) decreasing the ratio of total cholesterol/HDL cholesterol); (6) altering a body composition parameter ((a) increasing lean body mass; (b) decreasing trunk fat; (c) decreasing visceral fat; (d) decreasing abdominal girth; (e) decreasing visceral adipose tissue (VAT); and/or (f) decreasing the VAT/subcutaneous adipose tissue (SAT) ratio), (7) enhancing fertility or treating infertility (in women), treating lactation failure, (8) treating GH deficiency (e.g., GH deficiency with abdominal obesity), providing GH replacement therapy, e.g., in adults, treating idiopathic short stature (ISS) (9) treating GHRH receptor-related tumors, (10) treating hypothalamic pituitary dwarfism, (11) improving wound healing, (12) treating burns, (13) treating acute/chronic debilitating illness or infection, and/or (14) preventing/treating a condition characterized by deficient or decreased bone formation (e.g., osteoporosis); the method comprising administering an effective amount of a GHRH analog or salt thereof described herein or a composition comprising same (e.g., together with a pharmaceutically acceptable carrier/excipient), to a subject in need thereof.

"Treat", "treatment" or "treating" as used herein refer to application or administration to a subject, who has a disorder, a disease or a symptom of a disorder or a disease, with the purpose to cure, heal, alleviate, relieve, alter, remedy, ameliorate, improve, reduce the progression of or affect the disorder or disease and/or the symptoms of the disorder or disease. "Prevent", "prevention" or "preventing" as used herein refer to application or administration to a subject, who has a predisposition toward a disorder or disease or who is at risk of developing a disorder or disease, with the purpose to prevent or delay the onset of the disease or disorder or of the symptoms thereof, or reduce the severity of the disease or disorder or of the symptoms thereof, when administered prior to the onset or appearance of the disease or disorder or of the symptoms thereof.

"Subject" as used herein refers to warm blooded animals. In an embodiment, the subject is a mammal. In a further embodiment, the subject is a human. In an embodiment, the subject is an animal.

Dosage

An "effective amount" as used herein refers to an amount effective, at dosages and for periods of time necessary, to achieve the desired biological activity (e.g., inducing GH secretion) and/or the prophylactic/therapeutic result (e.g., prevention and/or treatment of the diseases and disorders noted above). A "therapeutically effective amount" as used herein refers to an effective amount in the context of therapy; a "prophylactically effective amount" refers to an effective amount in the context of prophylaxis. An effective amount of a compound or composition provided herein may vary according to factors such as the disease state, age, sex, and weight of the subject, and the ability of the compound or composition to elicit a desired response in the subject. Dosage regimens may be adjusted to provide the optimum prophylactic/therapeutic response. An effective amount is also one in which any toxic or detrimental effects of the compound are outweighed by the prophylactic/therapeutic beneficial effects.

The amount of GHRH analog needed depends on the type of pharmaceutical composition and on the mode of administration. In cases where human subjects receive solutions of a GHRH analog or salt thereof, administered by i.m. or s.c. injection, or in the form of intranasal spray or pulmonary inhalation, typical doses are between 2-20 mg/day, given once a day or divided into 2-4 administrations/day. When a GHRH analog or salt thereof is administered intravenously to human subjects, typical doses are in the range of 8-80 µg/kg of body weight/day, divided into 1-4 bolus injections/day or given as a continuous infusion. When depot preparations of a GHRH analog or salt thereof are used, e.g., by i.m. injection of palmitate salts or other salts of low solubility, or by i.m. or s.c. administration of microcapsules, microgranules, or implants containing a GHRH analog or salt thereof dispersed in a biodegradable polymer, typical doses are between 1-10 mg/day. In some embodiments, a GHRH analog or salt thereof is administered at a daily dose of about 0.1 mg to about 20 mg. In an embodiment, a GHRH analog or salt thereof is administered at a daily dose of about 1 mg or of about 2 mg.

Kits/Packages

Also provided herein are kits or packages comprising a GHRH analog or salt thereof described herein, or a composition comprising same. In an embodiment, the kit or package further comprises instructions for use, such as for inducing or stimulating the secretion of GH in a subject or for diagnosing, treating or preventing a GH-deficient condition. The kit or package may further comprise one or more containers.

EXAMPLES

The present invention is illustrated in further detail by the following non-limiting examples. The examples are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Abbreviations

The following abbreviations are used herein:
Abu: alpha amino butyric acid
Aib: aminoisobutyric acid
BHA: Benzhydrylamine resin
Boc: t-Butoxycarbony
COMU: 1-Cyano-2-ethoxy-2-oxoethylidenaminooxy)dimethylamino-morpholino-carbenium hexafluorophosphate
DI EA: Diisopropylethylamine
DMF: N,N-Dimethylformamide
EA: enzyme acceptor
ED: enzyme donor
EFC: enzyme fragment complementation
EIA: enzyme immunoassay
ELISA: enzyme-linked immunosorbent assay
FMOC: fluorenylmethoxycarbonyl
HCTU: 2-(6-Chloro-1H-benzotriazole-1-yl)-1,1,3,3-tetramethylaminium hexafluorophosphate,
HPLC: High Performance Liquid Chromatography
MALDI-TOF: Matrix Assisted Laser Desorption/Ionization Mass Spectrometry
Nle: L-norleucine
Orn: L-Ornithine
Har: L-HomoArginine
Pbf: 2,2,4,6,7-Pentamethyldihydrobenzofurane-5-sulfonyl
RLU: relative light units
RP-HPLC: Reverse Phase High Performance Liquid Chromatography
t-Bu: t-Butyl
TFA: Trifluoroacetic acid
Trt: Trityl Nomenclature The nomenclature used herein to define amino acid residues and synthetic peptides is that specified by the IUPAC-IUB Commission on Biochemical Nomenclature (European J. Biochem., 1984, 138, 9-37). By natural amino acid is meant one of the common naturally occurring amino acids found in proteins comprising Gly (G), Ala (A), Val (V), Leu (L), Ile (I), Ser (S), Thr (T), Lys (K), Arg (R), Asp (D), Asn (N), Glu (E), Gln (Q), Cys (C), Met (M), Phe (F), Tyr (Y), Pro (P), Trp (W) and His (H). Single letter codes are given in parentheses. Other abbreviations are Nle (norleucine), Aib (aminoisobutyric acid), Abu (alpha amino butyric acid), Orn (ornithine), and Har (HomoArginine). Lower case letters in the single letter code are used to indicate D-amino acids, for example "a" represents D-Ala.

Example 1: Materials and Methods

Synthesis and Preparation of GHRH Analogs

GHRH analogs described herein were made using a manual or an automated solid phase peptide synthesis approach using fluorenylmethoxycarbonyl-protected alpha-amino acids with appropriate side-chain protection and Benzhydrylamine (BHA) resin (Bachem AG) with a loading of 0.75 mmol/g. Before the coupling of amino acids, 6-aminohexanoic acid and Rink linker were coupled to the resin, and the Fmoc-[9H-fluoren-9-ylmethoxycarbonyl] protected amino acid was then coupled using [2-(6-Chloro-1H- benzotriazole-1-yl)-1,1,3,3-tetramethylaminium hexafluorophosphate] (HCTU) or (1-Cyano-2-ethoxy-2-oxoethylidenaminooxy)dimethylamino-morpholino-carbenium hexafluorophosphate (COMU), and diisopropylethylamine (DIEA) in N,N-Dimethylformamide (DMF) for about 1 hour. Fmoc deprotection was performed using 20% (v/v) piperidine in DMF for about 0.5 hour. A general procedure for N-capping the peptides described herein with acetyl was performed using acetic anhydride and DIEA. After completion of synthesis, peptides were cleaved from the solid phase support with simultaneous side-chain deprotection. Crude linear (also referred to as straight or unbranched) peptides were further purified by preparative RP-HPLC on C18-columns using acetonitrile gradient in 0.1% Trifluoroacetic acid (TFA). The peptides were vacuum-dried to remove acetonitrile and lyophilized from 0.1% TFA. Purity was assessed by analytical High Performance Liquid Chromatography (HPLC) and masses were determined by Matrix Assisted Laser Desorption/ionisation Mass Spectromety (MALDI-TOF MS) analysis using a Voyager™ instrument (PerSeptive Biosystems Inc.). GHRH Analogs 1-16 were prepared, as shown in Table 1.

TABLE 1

GHRH analogs prepared in this study

| Name | Sequence[1] | Average MW. | Purity (%) | SEQ ID No: |
|---|---|---|---|---|
| Analog 1 (C28) | YaDAIFTASYROVLAQLSAROALQDILC(Peg-2K)KN-NH$_2$ | 5342 | >95% | 9 |
| Analog 2 (C24) | YaDAIFTASYROVLAQLSAROALC(Peg-2K)DILSKN-NH$_2$ | 5301 | >95% | 10 |
| Analog 3 (C22) | YaDAIFTASYROVLAQLSAROC(Peg-2K)LQDILSKN-NH$_2$ | 5358 | >95% | 11 |
| Analog 4 (C19) | YaDAIFTASYROVLAQLSC(Peg-2K)ROALQDILSKN-NH$_2$ | 5358 | >95% | 12 |
| Analog 5 (C15) | YaDAIFTASYROVLC(Peg-2K)QLSAROALQDILSKN-NH$_2$ | 5358 | >95% | 13 |
| Analog 6 (C9) | YaDAIFTAC(Peg-2K)YROVLAQLSAROALQDILSKN-NH$_2$ | 5342 | >95% | 14 |
| Analog 7 (C8) | YaDAIFTC(Peg-2K)SYROVLAQLSAROALQDILSKN-NH$_2$ | 5358 | >95% | 15 |
| Analog 8 (C26) | YaDAIFTASYROVLAQLSAROALQDC(Peg-2K)LSKN-NH$_2$ | 5316 | >95% | 16 |
| Analog 9 (C16) | YaDAIFTASYROVLAC(Peg-2K)LSAROALQDILSKN-NH$_2$ | 5301 | >95% | 17 |
| Analog 10 (C9) | YaDAIFTAC(Peg-2K)YROVLAQLSAROALQDILS(Har)-NH$_2$ | 5278 | >95% | 18 |
| Analog 11 (C9,31) | YaDAIFTAC(Peg-2K)YROVLAQLSAROALQDILSRNC(Peg-2K)-NH$_2$ | 7474.0 | >95% | 19 |
| Analog 12 (C9,28) | YaDAIFTAC(Peg-2K)YROVLAQLSAROALQDILC(Peg-2K)RN-NH$_2$ | 7386.9 | >95% | 20 |
| Analog 13 (C9,24) | YaDAIFTAC(Peg-2K)YROVLAQLSAROALC(Peg-2K)DILSRN-NH$_2$ | 7345.9 | >95% | 21 |
| Analog 14 (C9,22) | YaDAIFTAC(Peg-2K)YROVLAQLSAROC(Peg-2K)LQDILSRN-NH$_2$ | 7402.9 | >95% | 22 |
| Analog 15 (C9) | YaDAIFTAC(Peg-5K)YROVLAQLSAROALQDILS(Har)-NH$_2$ | 8270.8 | >95% | 23 |
| Analog 16 (C9) | YaDAIFTAC(Peg-40K)YROVLAQLSAROALQDILS(Har)-NH$_2$ | 43270.8 | >95% | 24 |

[1] a = D-Alanine; O = L-Ornithine; Har = L-Homoarginine; C(Peg-2K) is Cys conjugated to a PEG polymer of about 2 kDa; C(Peg-5K) is Cys conjugated to a PEG polymer of less than or equal to about 5 kDa; C(Peg-40K) is Cys conjugated to a PEG polymer of about 40 kDa.

Example 2: Determination of the Agonist Potency of Pegylated GHRH Peptides in Cell Based Hit Hunter® (DiscoveRx™) Assay DiscoveRx™ has developed a panel of cell lines stably expressing non-tagged GPCRs that signal through cAMP. Hit Hunter® cAMP assays monitor the activation of a GPCR via Gs secondary messenger signaling in a homogenous, non-imaging assay format using a technology developed by DiscoveRx™ called Enzyme Fragment Complementation (EFC) with β-galactosidase (β-Gal) as the functional reporter.

cAMP Hunter™ cell lines were expanded from freezer stocks according to standard procedures. Cells were seeded in a total volume of 20 µL into white walled, 384-well microplates and incubated at 37° C. for the appropriate time prior to testing. cAMP modulation was determined using the DiscoveRx™ HitHunter™ cAMP XS+ assay. For agonist determination, cells were incubated with sample to induce response. Media was aspirated from cells and replaced with 15 µL 2:1 HBSS/10 mM Hepes: cAMP XS+Ab reagent. Intermediate dilution of sample stocks was performed to generate 4× sample in assay buffer. 4.5 µL of 4× sample was added to cells and incubated at 37° C. or room temperature for 30 or 60 minutes. Vehicle concentration was 1%. After appropriate compound incubation, assay signal was generated through incubation with 20 µL cAMP XS+ED/CL lysis cocktail for one hour followed by incubation with 20 µL cAMP XS+EA reagent for three hours at room temperature. Microplates were read following signal generation with a PerkinElmer Envision™ instrument for chemiluminescent signal detection. Compound activity was analyzed using CBIS data analysis suite (ChemInnovation, CA). For Gs agonist mode assays, percentage activity was calculated using the following formula: % Activity=100%×(mean RLU of test sample−mean RLU of vehicle control)/(mean RLU of MAX control−mean RLU of vehicle control). Results are shown in Table 2.

TABLE 2

Potency (% EC50 compared to baseline) and efficacy (Max response [%] compared to baseline) of GHRH analogs in a cell based assay specific to human GHRH receptor

| Name | SEQ ID No: | EC50 (nM) | Potency (%) | Max Response |
|---|---|---|---|---|
| GHRH$_{1-29}$ | 25 | 0.36 | 100 | 104.41 |
| Analog 1 (C28) | 9 | 0.29 | 125 | 105.09 |
| Analog 2 (C24) | 10 | 0.28 | 130 | 107.97 |
| Analog 3 (C22) | 11 | 0.25 | 143 | 100.17 |
| Analog 4 (C19) | 12 | 1.32 | 27 | 94.913 |
| Analog 5 (C15) | 13 | 1.38 | 26 | 106.95 |
| Analog 6 (C9) | 14 | 0.29 | 123 | 101.87 |
| Analog 7 (C8) | 15 | 0.69 | 52 | 108.48 |
| Analog 8 (C26) | 16 | 0.98 | 37 | 105.6 |
| Analog 9 (C16) | 17 | 0.92 | 39 | 107.12 |

The results showed that several Cys-PEG (2 kDa) substitutions at the 8, 15, 16, 19 and 26 positions were not tolerated and such peptides displayed reduced potency (e.g., Analogs 7, 5, 9, 4 and 8, respectively). This adverse effect was particularly evident in the N-terminal half of the peptide. Surprisingly, attachment of 2 kDa PEG at position 9 (Serine 9 in the native GHRH sequence) in the N-terminal part not only was well tolerated but increased the bioactivity of the peptide (Analog 6) by 123%. In contrast, PEGylation at position 8 (Asn in native GHRH sequence) was not tolerated (Analog 7).

PEGylation at positions 22 (Leu 22 in native GHRH), 24 (Gln 24 in native GHRH), and 28 (Ser 28 in native GHRH) also yielded peptides (Analogs 3, 2 and 1, respectively) with enhanced bioactivity compared to the native peptide (143%, 130%, 125%, respectively).

TABLE 3

Potency (% EC50 compared to baseline) and efficacy (Max response [%] compared to baseline) of GHRH analogs in a cell based assay specific to human GHRH receptor

| Name | SEQ ID No: | EC50 (nM) | Potency (%) | Max. response (%) |
|---|---|---|---|---|
| GHRH1-29 | 25 | 1.48 | 100 | 112.97 |
| Analog 10 (C9) | 18 | 0.11 | 1397 | 96.17 |
| Analog 11 (C9,31) | 19 | 0.47 | 314 | 97.17 |
| Analog 12 (C9,28) | 20 | 0.36 | 416 | 101.66 |
| Analog 13 (C9,24) | 21 | 0.41 | 361 | 103.49 |
| Analog 14 (C9,22) | 22 | 0.73 | 203 | 97.17 |
| Analog 15 (C9) | 23 | 0.22 | 669 | 94.34 |
| Analog 16 (C9) | 24 | 0.74 | 200 | 93.68 |

In an independent experiment, GHRH analogs containing 2 kDa (also referred to as 2K) PEG chains at positions 22, 24, 28 and 31 in addition to the $9^{th}$ position were produced and tested in the GHRH receptor cell based assay. Results are shown in Table 3 (analogs 14, 13, 12, and 11 respectively). The results showed that while retaining maximal efficacy, the doubly PEGylated peptides also were 2-4 fold more potent than the native peptide.

We also explored the length of the PEG chain that can be tolerated at the $9^{th}$ position by producing GHRH analogs containing 5 kDa (also referred to as 5K) and 40 kDa (also referred to as 40K) PEG chains (analogs 15 and 16 respectively). In vitro testing showed that longer PEG chains can be attached at the $9^{th}$ position without loss of in vitro biological activity, in contrast to the results in vivo (see example 3). However, the analog containing 2K PEG (analog 10) was almost 14-fold more potent than the native peptide and 2-6 fold more potent than the 5K and 40K Pegylated GHRH peptides (analogs 15 and 16 respectively).

Example 3: GH Release Kinetics in Response to Subcutaneous Injection of Selected GHRH Analogs in Sprague-Dawley Rats Protocol:

Sprague-Dawley rats (female, weighing from 250 to 300 g) were obtained from Charles River Inc. Animals were used according to a protocol of the Animal Care Committee along with the principles of the Guide for the Care and Use of Experimental Animals of the Canadian Council on Animal Care. The animals were maintained on standard laboratory chow under a 12:12 light:dark cycle. They were kept in groups of 4 rats per cage. The animals were anesthetized with isoflurane 2.5%. A mid-section opening was made in the neck to expose the carotid artery. The carotid artery was canulated with polypropylene tubing (PE-50) to allow blood withdrawal. After surgical preparation, rats received a subcutaneous injection of GHRH analog (10-100 µg/kg) dissolved in 20 mM AcONa+5% mannitol at pH 5). Blood samples (400 µL/time point) were collected from 2-4 animals per group. Blood samples were collected via the carotid catheter at 0, 10, 20, 30, 45 and 60 minutes after drug injection. Blood was collected into microtainer tubes containing K3EDTA, mixed and immediately centrifuged at 13,000 RPM in a desktop centrifuge for 2 minutes. The plasma was collected and placed into a screw cap Eppendorf™ tube and quickly frozen in liquid nitrogen. The samples were then kept at −80° C. until assayed. Determination of GH levels was performed as described below.

Determination of GH Levels in Plasma Samples:

Rat and mouse plasma samples were vortexed carefully and centrifuged at 9,000 RPM for 2 min at 4° C. The dosage of GH levels was performed using the Rat/Mouse Growth Hormone ELISA kit from Millipore™ (Cat. # EZRMGH-45K). Sample supernatants were first diluted 20-fold with the GH ELISA assay buffer, and 10 µl of this dilution was added to the ELISA plate with 90 µl of GH EIA assay buffer. The remainder of the procedure was performed according to the manufacturer's instructions, and the data obtained were analyzed using GraphPad Prism™ software. Three peptides containing PEG2K chains at the $8^{th}$, $9^{th}$ and $28^{th}$ position in the GHRH peptide were injected subcutaneously at a single dose of 0.04 mg/kg. Growth hormone levels were determined in timed-aliquots of blood and are depicted in FIG. 1. Attachment of PEG2K in the C-terminal part of the GHRH peptide (at position 28) potently stimulated GH secretion. As expected from the potency results in the cell-based assay, PEG2K attachment at position 9 (Cmax: 651 ng/ml; AUC (0-90 min): 29075 ng/ml/90 min), but not at position 8 (Cmax: 397 ng/ml, AUC (0-90 min) 15657 ng/ml/90 min) produced greater stimulation of GH secretion in rats. These in vivo results corroborate the in vitro biological assays and highlight the $9^{th}$ 43370-003 amino acid position in the GHRH sequence as a position that can tolerate short PEG chain attachment without significant impact on biological activity of the peptide.

Figure 2:
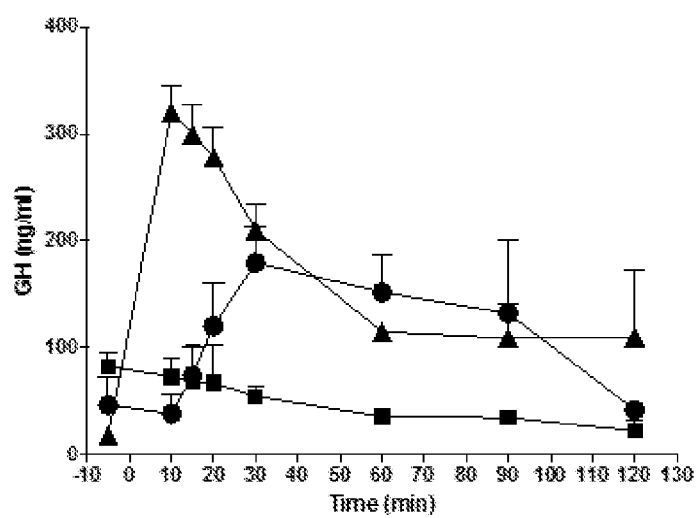
FIG. 2 is a graph showing stimulation of Growth Hormone secretion vs. time after administration by peptides containing PEG2K chains at the $9^{th}$ position (Analog 10-Triangles), PEG5K chains at the $9^{th}$ position (Analog 15—Circles) and PEG40K chains at the $9^{th}$ position (Analog 16—Squares).

The N-terminal part of the GHRH peptide is known to be buried in the extracellular loops and transmembrane domains of the GHRH receptor, and thus almost all of the amino acids in the N-terminal domain participate in high affinity binding of the GHRH peptide to the receptor. Felix et al (1995) have shown that covalent attachment of PEG (2K and 5K) at Asn8 and Lys12 (which are in the N-terminal domain of GHRH) results in reduction of biological activity of GHRH. Therefore, it was surprising that GHRH peptides having pegylation with PEG2K at the $9^{th}$ amino acid retained full biological activity in vitro and in vivo. In order to see what length of PEG chain can be attached at the $9^{th}$ amino acid before biological activity is hampered, peptides containing 2K, 5K and 40K PEG chains were synthesized and tested in female rats using the protocol described above. Briefly, peptides (0.04 mg/kg) were subcutaneously injected in female rats and growth hormone levels were determined in timed aliquots of blood drawn from the animals. The results are shown in FIG. 2. Peptides having 5K and higher length PEG chains produced significantly less growth hormone than peptide containing 2K PEG chain at the $9^{th}$ amino acid position. This experiment demonstrated that PEG chains longer than 5K may not be tolerated at the $9^{th}$ amino acid position of GHRH as well as shorter PEG chains.

Sequences of peptides described herein are shown in Table 4. In Table 4, X1, X2, X8, X9, X11, X12, X15, X18, X20, X21, X22, X24, X25, X26, X27, X28, X29, X30, C(Peg-5K, C(Peg-2K) and C(Peg-40K) are as described herein; a is D-Alanine; 0 is L-Ornithine; Har is L-Homoarginine; and Z is Lys, Arg, Har or Agmantine.

TABLE 4

Sequences of peptides described herein

| Name | Peptide Sequence | SEQ ID NO: |
|---|---|---|
| Formula (I) | X1-X2-D-A-I-F-T-X8-X9-Y-X11-X12-V-L-X15-Q-L-X18-A-X20-X21-X22-L-X24-X25-X26-X27-X28-X29-X30 | 1 |
| Peptide C9 | YaDAIFTAC(Peg-5K)YROVLAQLSAROALQDILSZ | 2 |
| Peptide C22 | YaDAIFTASYROVLAQLSAROC(Peg-5K)LQDILSZ | 3 |
| Peptide C24 | YaDAIFTASYROVLAQLSAROALC(Peg-5K)DILSZ | 4 |
| Peptide C28 | YaDAIFTASYROVLAQLSAROALQDILC(Peg-5K)Z | 5 |
| Peptide C(9,22) | YaDAIFTAC(Peg-5K)YROVLAQLSAROC(Peg-5K)LQDILSZ | 6 |
| Peptide C(9,24) | YaDAIFTAC(Peg-5K)YROVLAQLSAROALC(Peg-5K)DILSZ | 7 |
| Peptide C(9,28) | YaDAIFTAC(Peg-5K)YROVLAQLSAROALQDILC(Peg-5K)Z | 8 |
| Analog 1 (C28) | YaDAIFTASYROVLAQLSAROALQDILC(Peg-2K)KN-NH$_2$ | 9 |
| Analog 2 (C24) | YaDAIFTASYROVLAQLSAROALC(Peg-2K)DILSKN-NH$_2$ | 10 |
| Analog 3 (C22) | YaDAIFTASYROVLAQLSAROC(Peg-2K)LQDILSKN-NH$_2$ | 11 |

TABLE 4-continued

Sequences of peptides described herein

| Name | Peptide Sequence | SEQ ID NO: |
|---|---|---|
| Analog 4 (C19) | YaDAIFTASYROVLAQLSC(Peg-2K)ROALQDILSKN-NH$_2$ | 12 |
| Analog 5 (C15) | YaDAIFTASYROVLC(Peg-2K)QLSAROALQDILSKN-NH$_2$ | 13 |
| Analog 6 (C9) | YaDAIFTAC(Peg-2K)YROVLAQLSAROALQDILSKN-NH$_2$ | 14 |
| Analog 7 (C8) | YaDAIFTC(Peg-2K)SYROVLAQLSAROALQDILSKN-NH$_2$ | 15 |
| Analog 8 (C26) | YaDAIFTASYROVLAQLSAROALQDC(Peg-2K)LSKN-NH$_2$ | 16 |
| Analog 9 (C16) | YaDAIFTASYROVLAC(Peg-2K)LSAROALQDILSKN-NH$_2$ | 17 |
| Analog 10 (C9) | YaDAIFTAC(Peg-2K)YROVLAQLSAROALQDILS-(Har)-NH$_2$ | 18 |
| Analog 11 (C9,31) | YaDAIFTAC(Peg-2K)YROVLAQLSAROALQDILSRNC(Peg-2K)-NH$_2$ | 19 |
| Analog 12 (C9, 28) | YaDAIFTAC(Peg-2K)YROVLAQLSAROALQDILC(Peg-2K)RN-NH$_2$ | 20 |
| Analog 13 (C9,24) | YaDAIFTAC(Peg-2K)YROVLAQLSAROALC(Peg-2K)DILSRN-NH$_2$ | 21 |
| Analog 14 (C9,22) | YaDAIFTAC(Peg-2K)YROVLAQLSAROC(Peg-2K)LQDILSRN-NH$_2$ | 22 |
| Analog 15 (C9) | YaDAIFTAC(Peg-5K)YROVLAQLSAROALQDILS(Har)-NH$_2$ | 23 |
| Analog 16 (C9) | YaDAIFTAC(Peg-40K)YROVLAQLSAROALQDILS(Har)-NH$_2$ | 24 |
| Human GHRH$_{1-29}$ | YADAIFTNSYRKVLGQLSARKLLQDIMSR-NH$_2$ | 25 |
| Human GHRH$_{1-44}$ | YADAIFTNSYRKVLGQLSARKLLQDIMSRQQGESNQERGARARL-NH$_2$ | 26 |
| Human GHRH$_{30-44}$ | QQGESNQERGARARL | 27 |

The foregoing is illustrative of the present invention and is not to be construed as limiting thereof. Although the present invention has been described hereinabove by way of specific embodiments thereof, those skilled in the art will readily appreciate that many modifications are possible in the exemplary embodiments without materially departing from the teachings and advantages of this invention. Accordingly, all such modifications are intended to be included within the scope of this invention as defined in the claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

Baca et al., J. Am. Chem. Soc. 117: 1881-1887, 1995.
Bokser L et al. 1990. Life Sci. 46(14): 999-1005.
Campbell R M et al. 1991. Peptides. 12(3): 569-574.
Campbell R M et al. 1994. Peptides. 15(3): 489-495.
Campbell, R M et al. 1992. Peptides. 13(4):787-793.
Campbell, R M et al. 1997. J Pept Res. 49(6): 527-537.
Cervini L A et al. 1998. J Med Chem. 41(5):717-727.
Digilio G et al. 2003. J. Am. Chem. Soc. 125(12): 3458-70.
Esposito P et al. 2003. Adv. Drug Deliv. Rev. 55(10): 1279-91.
Felix, A M et al. 1988. Int J Pept Res. 32(6): 441-454.
Felix, A M et al. 1995. Int J Pept Protein Res. 46(3-4): 253-64.
Freidman A R et al. 1991. Int J Pept Res. 37(1): 14-20.
Frohman et al. 1986b. J Clin Invest. 78(4):906-13.
Frohman L A et al. 1986a. Endocr. Rev. 7 223-233.
Frohman L A et al. 1989. J Clin Invest. 83(5):1533-40.
Gao, et al. 1994. Life Science 54: 247-252.
Gololobov, G et al. 1998. J Pharmacol. Expt Therapeut. 285(2): 753-758)
Hodate K et al. 1986. Endocrinol. Jpn. 33(4): 519-525.
Kovacs M et al. 1988. Life Sci. 42(1): 27-35.
Kubiak, T M et al. 1993. J Med Chem. 36(7): 888-897.

Ling N, et al. 1984b. Biochem. Biophys. Res. Commun. 122(1): 304-10.
Ling N. et al. 1984a. Biochem. Biophys. Res. Commun. 123(2): 854-861.
Liu and Tam, J. Am. Chem. Soc. 116: 4149-4153, 1994a.
Liu and Tam, Proc. Natl. Acad. Sci. USA 91: 6584-6588, 1994b.
Liu et al., Tetrahedron Lett. 37: 933-936, 1996.
Lu Y A et al. 1993, Pept. Res. 6(3): 140-6.
Lu Y A et al. 1994, Int. J. Peptide Protein Res. 43(2): 127-38.
Murphy W A et al. 1988. J Pept Res. 1(1): 36-41.
Nakagawa et al., J. Am. Chem. Soc. 107: 7087-7092, 1985.
Sato, K et al. 1987. Biochem. Biophys. Res. Commun. 149(2): 531-7;
Sato, K et al. 1990. Biochem. Biophys. Res. Commun. 167(1): 360-366.
Schnolzer and Kent, Science 256: 221-225, 1992.
Tam et al., Int. J. Peptide Protein Res. 45: 209-216, 1995.
Yamashiro and Li, Int. J. Peptide Protein Res. 31: 322-334, 1988).
Youn, Y S and Lee, K C 2007. Bioconjug. Chem. 18(2): 500-6.
Zarandi, M et al. 1990. Int J Pept Res. 36(6): 499-505.
Zarandi, M et al. 1992. Int J Pept Res. 39(3): 211-217.
Zarandi, M et al. 1994. Proc Natl Acad Sci USA. 91(25): 12298-12302.

What is claimed is:

1. A growth hormone releasing hormone (GHRH) analog comprising a peptide having the sequence set forth in formula (I) (SEQ ID NO: 1):

(I)
X1-X2-Asp-Ala-Ile-Phe-Thr-X8-X9-Tyr-X11-X12-Val-

Leu-X15-Gln-Leu-X18-Ala-X20-X21-X22-Leu-X24-X25-

X26-X27-X28-X29-X30 wherein:
X1 is Tyr, His, N-methyl Tyr or Desamino Tyr;
X2 is Ala, D-Ala, Ser or alpha aminoisobutyric acid (Aib);
X8 is Asn, Asp, Ala, Gln, Ser or Aib;
X9 is Cys conjugated to a PEG polymer of less than or equal to 5 kDa;
X11 is Arg or L-Homoarginine (Har);
X12 is Lys or Orn;
X15 is Gly or Ala;
X18 is Ser or Ala;
X20 is Arg or Har;
X21 is Lys or Orn;
X22 is Leu, Val, Ala or Cys conjugated to a PEG polymer of less than or equal to 5 kDa;
X24 is Gln or Cys conjugated to a PEG polymer of less than or equal to 5 kDa;
X25 is Asp or Ala;
X26 is Ile or Ala;
X27 is Met, Leu or Norleucine;
X28 is Ser, Ala or Cys conjugated to a PEG polymer of less than or equal to 5 kDa;
X29 is Lys, Arg, Orn, Har or Agmatine; and
X30 is an NH$_2$ group or Asn-NH$_2$;
or a pharmaceutically acceptable salt thereof.

2. The GHRH analog or salt thereof of claim 1, wherein at least one of X22, X24 and X28 is Cys conjugated to a PEG polymer of less than or equal to 5 kDa.

3. The GHRH analog or salt thereof of claim 1, wherein X22 is Cys conjugated to a PEG polymer of less than or equal to 5 kDa.

4. The GHRH analog or salt thereof of claim 1, wherein X24 is Cys conjugated to a PEG polymer of less than or equal to 5 kDa.

5. The GHRH analog or salt thereof of claim 1, wherein X28 is Cys conjugated to a PEG polymer of less than or equal to 5 kDa.

6. The GHRH analog or salt thereof of claim 1, wherein the PEG polymer of less than or equal to 5 kDa is a PEG polymer of 2 kDa.

7. The GHRH analog or salt thereof of claim 1, wherein said GHRH analog or salt thereof is:

```
                                          (SEQ ID NO: 14)
YaDAIFTAC(Peg-2K)YROVLAQLSAROALQDILSKN-NH2;

(SEQ ID NO: 18);
YaDAIFTAC(Peg-2K)YROVLAQLSAROALQDILS-(Har)-NH2;

(SEQ ID NO: 20)
YaDAIFTAC(Peg-2K)YROVLAQLSAROALQDILC(Peg-2K)RN-
NH2;

(SEQ ID NO: 21)
YaDAIFTAC(Peg-2K)YROVLAQLSAROALC(Peg-2K)DILSRN-
NH2;
or (SEQ ID NO: 22)
YaDAIFTAC(Peg-2K)YROVLAQLSAROC(Peg-2K)LQDILSRN-
NH2;
``` wherein a is D-Ala, O is L-Ornithine (Orn), Har is L-Homoarginine and C(Peg-2K) is Cys conjugated to a PEG polymer of 2 kDa;
or a pharmaceutically acceptable salt thereof.

8. The GHRH analog or salt thereof of claim 7, wherein said GHRH analog or salt thereof is:

```
                                          (SEQ ID NO: 14)
   YaDAIFTAC(Peg-2K)YROVLAQLSAROALQDILSKN-NH2.
```

9. The GHRH analog or salt thereof of claim 7, wherein said GHRH analog or salt thereof is:

```
                                          (SEQ ID NO: 18)
YaDAIFTAC(Peg-2K)YROVLAQLSAROALQDILS-(Har)-NH2.
```

10. The GHRH analog or salt thereof of claim 7, wherein said GHRH analog or salt thereof is:

```
                                          (SEQ ID NO: 20)
YaDAIFTAC(Peg-2K)YROVLAQLSAROALQDILC(Peg-2K)RN-
NH2.
```

11. The GHRH analog or salt thereof of claim 7, wherein said GHRH analog or salt thereof is:

```
                                          (SEQ ID NO: 21)
YaDAIFTAC(Peg-2K)YROVLAQLSAROALC(Peg-2K)DILSRN-
NH2.
```

12. The GHRH analog or salt thereof of claim 7, wherein said GHRH analog or salt thereof is:

```
                                          (SEQ ID NO: 22)
YaDAIFTAC(Peg-2K)YROVLAQLSAROC(Peg-2K)LQDILSRN-
NH2.
```

13. A pharmaceutical composition comprising the GHRH analog or salt thereof of claim 1.

14. The pharmaceutical composition of claim 13, further comprising one or more pharmaceutically acceptable carriers, excipients, and/or diluents.

15. A method for inducing growth hormone secretion in a subject in need thereof, comprising administering to the subject an effective amount of the GHRH analog or salt thereof of claim 1.

16. A method for treating, preventing, or diagnosing a GH-deficient condition in a subject in need thereof, comprising administering to the subject an effective amount of the GHRH analog or salt thereof of claim 1.

17. The method of claim 15, wherein said GHRH analog of salt thereof is administered at a daily dose of 0.1 mg to 10 mg.

18. The method of claim 15, wherein said GHRH analog or salt thereof is administered by an intravenous, oral, transdermal, subcutaneous, mucosal, intramuscular, intranasal, or pulmonary route.

19. The method of claim 16, wherein said GHRH analog of salt thereof is administered at a daily dose of 0.1 mg to 10 mg.

20. The method of claim 16, wherein said GHRH analog or salt thereof is administered by an intravenous, oral, transdermal, subcutaneous, mucosal, intramuscular, intranasal, or pulmonary route.

* * * * *

SEQUENCE LISTING

```
<160> NUMBER OF SEQ ID NOS: 27

<210> SEQ ID NO 1
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa at position 1 is Tyr, His, N-methyl
      Tyrosine, or Desamino Tyr
<220> FEATURE:
<221> NAME/KEY: misc_feature
<222> LOCATION: (2)..(2)
<223> OTHER INFORMATION: Xaa at position 2 is Ala, D-Ala, Ser, or
      alpha aminoisobutyric acid (Aib)
<220> FEATURE:
<221> NAME/KEY: misc_feature
<222> LOCATION: (8)..(8)
<223> OTHER INFORMATION: Xaa at position 8 is Asn, Asp, Ala, Gln, Ser or
      Aib
<220> FEATURE:
<221> NAME/KEY: misc_feature
<222> LOCATION: (9)..(9)
<223> OTHER INFORMATION: Xaa at position 9 is Ser, Asp, Ala, or Cys
      conjugated to a PEG polymer of less than or equal to about 5 kDa
<220> FEATURE:
<221> NAME/KEY: misc_feature
<222> LOCATION: (11)..(11)
<223> OTHER INFORMATION: Xaa at position 11 is Arg or L-Homoarginine
      (Har)
<220> FEATURE:
<221> NAME/KEY: misc_feature
<222> LOCATION: (12)..(12)
<223> OTHER INFORMATION: Xaa at position 12 is Lys or L-Ornithine (Orn);
<220> FEATURE:
<221> NAME/KEY: misc_feature
<222> LOCATION: (15)..(15)
<223> OTHER INFORMATION: Xaa at position 15 is Gly or Ala
<220> FEATURE:
<221> NAME/KEY: misc_feature
<222> LOCATION: (18)..(18)
<223> OTHER INFORMATION: Xaa at position 18 is Ser or Ala
<220> FEATURE:
<221> NAME/KEY: misc_feature
<222> LOCATION: (20)..(20)
<223> OTHER INFORMATION: Xaa at position 20 is Arg or Har
<220> FEATURE:
<221> NAME/KEY: misc_feature
<222> LOCATION: (21)..(21)
<223> OTHER INFORMATION: Xaa at position 21 is Lys or Orn
<220> FEATURE:
<221> NAME/KEY: misc_feature
<222> LOCATION: (22)..(22)
<223> OTHER INFORMATION: Xaa at position 22 is Leu, Val, Ala, or Cys
      conjugated to a PEG polymer of less than or equal to about 5 kDa
<220> FEATURE:
<221> NAME/KEY: misc_feature
```

```
<222> LOCATION: (24)..(24)
<223> OTHER INFORMATION: Xaa at position 24 is Gln or Cys conjugated to
      a PEG polymer of less than or equal to about 5 kDa
<220> FEATURE:
<221> NAME/KEY: misc_feature
<222> LOCATION: (25)..(25)
<223> OTHER INFORMATION: Xaa at position 25 is Asp or Ala
<220> FEATURE:
<221> NAME/KEY: misc_feature
<222> LOCATION: (26)..(26)
<223> OTHER INFORMATION: Xaa at position 26 is Ile or Ala
<220> FEATURE:
<221> NAME/KEY: misc_feature
<222> LOCATION: (27)..(27)
<223> OTHER INFORMATION: Xaa at position 27 is Met, Leu or Norleucine
<220> FEATURE:
<221> NAME/KEY: misc_feature
<222> LOCATION: (28)..(28)
<223> OTHER INFORMATION: Xaa at position 28 is Ser, Ala or Cys
      conjugated to a PEG polymer of less than or equal to about 5 kDa
<220> FEATURE:
<221> NAME/KEY: misc_feature
<222> LOCATION: (29)..(29)
<223> OTHER INFORMATION: Xaa at position 29 is Lys, Arg, Orn, Har or
      Agmantine
<220> FEATURE:
<221> NAME/KEY: misc_feature
<222> LOCATION: (30)..(30)
<223> OTHER INFORMATION: Xaa at position 30 is Asn-NH2 or an NH2 group

<400> SEQUENCE: 1

Xaa Xaa Asp Ala Ile Phe Thr Xaa Xaa Tyr Xaa Xaa Val Leu Xaa Gln
1               5                   10                  15

Leu Xaa Ala Xaa Xaa Xaa Leu Xaa Xaa Xaa Xaa Xaa Xaa Xaa
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of less than or equal to about 5 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 12 is L-Ornithine
<220> FEATURE:
<221> NAME/KEY: misc_feature
<222> LOCATION: (29)..(29)
<223> OTHER INFORMATION: Xaa at position 29 is Lys, Arg, L-Homoarginine
      or Agmantine

<400> SEQUENCE: 2

Tyr Xaa Asp Ala Ile Phe Thr Ala Xaa Tyr Arg Xaa Val Leu Ala Gln
1               5                   10                  15

Leu Ser Ala Arg Xaa Ala Leu Gln Asp Ile Leu Ser Xaa
            20                  25

<210> SEQ ID NO 3
<211> LENGTH: 29
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (22)..(22)
<223> OTHER INFORMATION: Xaa at position 22 is Cys conjugated to a PEG
      polymer of less than or equal to about 5 kDa
<220> FEATURE:
<221> NAME/KEY: misc_feature
<222> LOCATION: (29)..(29)
<223> OTHER INFORMATION: Xaa at position 29 is Lys, Arg, L-Homoarginine
      or Agmantine

<400> SEQUENCE: 3

Tyr Xaa Asp Ala Ile Phe Thr Ala Ser Tyr Arg Xaa Val Leu Ala Gln
1               5                   10                  15

Leu Ser Ala Arg Xaa Xaa Leu Gln Asp Ile Leu Ser Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (24)..(24)
<223> OTHER INFORMATION: Xaa at position 24 is Cys conjugated to a PEG
      polymer of less than or equal to about 5 kDa
<220> FEATURE:
<221> NAME/KEY: misc_feature
<222> LOCATION: (29)..(29)
<223> OTHER INFORMATION: Xaa at position 29 is Lys, Arg, L-Homoarginine
      or Agmantine

<400> SEQUENCE: 4

Tyr Xaa Asp Ala Ile Phe Thr Ala Ser Tyr Arg Xaa Val Leu Ala Gln
1               5                   10                  15

Leu Ser Ala Arg Xaa Ala Leu Xaa Asp Ile Leu Ser Xaa
            20                  25

<210> SEQ ID NO 5
<211> LENGTH: 29
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (28)..(28)
<223> OTHER INFORMATION: Xaa at position 28 is Cys conjugated to a PEG
      polymer of less than or equal to about 5 kDa
<220> FEATURE:
<221> NAME/KEY: misc_feature
<222> LOCATION: (29)..(29)
<223> OTHER INFORMATION: Xaa at position 29 is Lys, Arg, L-Homoarginine
      or Agmantine

<400> SEQUENCE: 5

Tyr Xaa Asp Ala Ile Phe Thr Ala Ser Tyr Arg Xaa Val Leu Ala Gln
1               5                   10                  15

Leu Ser Ala Arg Xaa Ala Leu Gln Asp Ile Leu Xaa Xaa
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of less than or equal to about 5 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (22)..(22)
<223> OTHER INFORMATION: Xaa at position 22 is Cys conjugated to a PEG
      polymer of less than or equal to about 5 kDa
<220> FEATURE:
<221> NAME/KEY: misc_feature
<222> LOCATION: (29)..(29)
<223> OTHER INFORMATION: Xaa at position 29 is Lys, Arg, L-Homoarginine
      or Agmantine

<400> SEQUENCE: 6

Tyr Xaa Asp Ala Ile Phe Thr Ala Xaa Tyr Arg Xaa Val Leu Ala Gln
1               5                   10                  15

Leu Ser Ala Arg Xaa Xaa Leu Gln Asp Ile Leu Ser Xaa
            20                  25

<210> SEQ ID NO 7
<211> LENGTH: 29
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of less than or equal to about 5 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (24)..(24)
<223> OTHER INFORMATION: Xaa at position 24 is Cys conjugated to a PEG
      polymer of less than or equal to about 5 kDa
<220> FEATURE:
<221> NAME/KEY: misc_feature
<222> LOCATION: (29)..(29)
<223> OTHER INFORMATION: Xaa at position 29 is Lys, Arg, L-Homoarginine
      or Agmantine

<400> SEQUENCE: 7

Tyr Xaa Asp Ala Ile Phe Thr Ala Xaa Tyr Arg Xaa Val Leu Ala Gln
1               5                   10                  15

Leu Ser Ala Arg Xaa Ala Leu Xaa Asp Ile Leu Ser Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of less than or equal to about 5 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (28)..(28)
<223> OTHER INFORMATION: Xaa at position 28 is Cys conjugated to a PEG
      polymer of less than or equal to about 5 kDa
<220> FEATURE:
<221> NAME/KEY: misc_feature
<222> LOCATION: (29)..(29)
<223> OTHER INFORMATION: Xaa at position 29 is Lys, Arg, L-Homoarginine
      or Agmantine

<400> SEQUENCE: 8

Tyr Xaa Asp Ala Ile Phe Thr Ala Xaa Tyr Arg Xaa Val Leu Ala Gln
1               5                   10                  15
```

Leu Ser Ala Arg Xaa Ala Leu Gln Asp Ile Leu Xaa Xaa
            20                  25

<210> SEQ ID NO 9
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (28)..(28)
<223> OTHER INFORMATION: Xaa at position 28 is Cys conjugated to a PEG
      polymer of about 2 kDa
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 9

Tyr Xaa Asp Ala Ile Phe Thr Ala Ser Tyr Arg Xaa Val Leu Ala Gln
1               5                   10                  15

Leu Ser Ala Arg Xaa Ala Leu Gln Asp Ile Leu Xaa Lys Xaa
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (24)..(24)
<223> OTHER INFORMATION: Xaa at position 24 is Cys conjugated to a PEG
      polymer of about 2 kDa
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 10

Tyr Xaa Asp Ala Ile Phe Thr Ala Ser Tyr Arg Xaa Val Leu Ala Gln
1               5                   10                  15

Leu Ser Ala Arg Xaa Ala Leu Xaa Asp Ile Leu Ser Lys Xaa
            20                  25                  30

```
<210> SEQ ID NO 11
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (22)..(22)
<223> OTHER INFORMATION: Xaa at position 22 is Cys conjugated to a PEG
      polymer of about 2 kDa
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 11

Tyr Xaa Asp Ala Ile Phe Thr Ala Ser Tyr Arg Xaa Val Leu Ala Gln
1               5                   10                  15

Leu Ser Ala Arg Xaa Xaa Leu Gln Asp Ile Leu Ser Lys Xaa
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (19)..(19)
<223> OTHER INFORMATION: Xaa at position 19 is Cys conjugated to a PEG
      polymer of about 2 kDa
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 12

Tyr Xaa Asp Ala Ile Phe Thr Ala Ser Tyr Arg Xaa Val Leu Ala Gln
1               5                   10                  15

Leu Ser Xaa Arg Xaa Ala Leu Gln Asp Ile Leu Ser Lys Xaa
            20                  25                  30

<210> SEQ ID NO 13
<211> LENGTH: 30
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (15)..(15)
<223> OTHER INFORMATION: Xaa at position 15 is Cys conjugated to a PEG
      polymer of about 2 kDa
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 13

Tyr Xaa Asp Ala Ile Phe Thr Ala Ser Tyr Arg Xaa Val Leu Xaa Gln
1               5                   10                  15
Leu Ser Ala Arg Xaa Ala Leu Gln Asp Ile Leu Ser Lys Xaa
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of about 2 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 14

Tyr Xaa Asp Ala Ile Phe Thr Ala Xaa Tyr Arg Xaa Val Leu Ala Gln
1               5                   10                  15
Leu Ser Ala Arg Xaa Ala Leu Gln Asp Ile Leu Ser Lys Xaa
            20                  25                  30

<210> SEQ ID NO 15
<211> LENGTH: 30
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (8)..(8)
<223> OTHER INFORMATION: Xaa at position 8 is Cys conjugated to a PEG
      polymer of about 2 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 15

Tyr Xaa Asp Ala Ile Phe Thr Xaa Ser Tyr Arg Xaa Val Leu Ala Gln
1               5                   10                  15

Leu Ser Ala Arg Xaa Ala Leu Gln Asp Ile Leu Ser Lys Xaa
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (26)..(26)
<223> OTHER INFORMATION: Xaa at position 26 is Cys conjugated to a PEG
      polymer of about 2 kDa
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 16

Tyr Xaa Asp Ala Ile Phe Thr Ala Ser Tyr Arg Xaa Val Leu Ala Gln
1               5                   10                  15

Leu Ser Ala Arg Xaa Ala Leu Gln Asp Xaa Leu Ser Lys Xaa
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (2)..(2)
<223> OTHER INFORMATION: Xaa at position 2 is D-Ala
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (16)..(16)
<223> OTHER INFORMATION: Xaa at position 16 is Cys conjugated to a PEG
      polymer of about 2 kDa
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 17

Tyr Xaa Asp Ala Ile Phe Thr Ala Ser Tyr Arg Xaa Val Leu Ala Xaa
1               5                   10                  15

Leu Ser Ala Arg Xaa Ala Leu Gln Asp Ile Leu Ser Lys Xaa
            20                  25                  30

<210> SEQ ID NO 18
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of about 2 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (29)..(29)
<223> OTHER INFORMATION: Xaa at position 29 is L-Homoarginine modified
      at the carboxy-terminal with NH2

<400> SEQUENCE: 18

Tyr Xaa Asp Ala Ile Phe Thr Ala Xaa Tyr Arg Xaa Val Leu Ala Gln
1               5                   10                  15

Leu Ser Ala Arg Xaa Ala Leu Gln Asp Ile Leu Ser Xaa
            20                  25

<210> SEQ ID NO 19
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
```

```
<221> NAME/KEY: misc_feature
<222> LOCATION: (9)..(9)
<223> OTHER INFORMATION: Xaa at position 9 is Cys conjugated to a PEG
      polymer of about 2 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (31)..(31)
<223> OTHER INFORMATION: Xaa at position 31 is Cys conjugated to a PEG
      polymer of about 2 kDa and modified at the carboxy-terminal with
      NH2

<400> SEQUENCE: 19

Tyr Xaa Asp Ala Ile Phe Thr Ala Xaa Tyr Arg Xaa Val Leu Ala Gln
1               5                   10                  15

Leu Ser Ala Arg Xaa Ala Leu Gln Asp Ile Leu Ser Arg Asn Xaa
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of about 2 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (28)..(28)
<223> OTHER INFORMATION: Xaa at position 28 is Cys conjugated to a PEG
      polymer of about 2 kDa
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 20

Tyr Xaa Asp Ala Ile Phe Thr Ala Xaa Tyr Arg Xaa Val Leu Ala Gln
1               5                   10                  15

Leu Ser Ala Arg Xaa Ala Leu Gln Asp Ile Leu Xaa Arg Xaa
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of about 2 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (24)..(24)
<223> OTHER INFORMATION: Xaa at position 24 is Cys conjugated to a PEG
      polymer of about 2 kDa
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 21

Tyr Xaa Asp Ala Ile Phe Thr Ala Xaa Tyr Arg Xaa Val Leu Ala Gln
1               5                   10                  15

Leu Ser Ala Arg Xaa Ala Leu Xaa Asp Ile Leu Ser Arg Xaa
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of about 2 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (22)..(22)
<223> OTHER INFORMATION: Xaa at position 22 is Cys conjugated to a PEG
      polymer of about 2 kDa
<220> FEATURE:
<221> NAME/KEY: misc_feature
<222> LOCATION: (30)..(30)
<223> OTHER INFORMATION: Xaa at position 30 is Asn modified at the
      carboxy-terminal with NH2

<400> SEQUENCE: 22

Tyr Xaa Asp Ala Ile Phe Thr Ala Xaa Tyr Arg Xaa Val Leu Ala Gln
1               5                   10                  15

Leu Ser Ala Arg Xaa Xaa Leu Gln Asp Ile Leu Ser Arg Xaa
            20                  25                  30

<210> SEQ ID NO 23
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of less than or equal to about 5 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (29)..(29)
<223> OTHER INFORMATION: Xaa at position 29 is L-Homoarginine modified
      at the carboxy-terminal with NH2

<400> SEQUENCE: 23

Tyr Xaa Asp Ala Ile Phe Thr Ala Xaa Tyr Arg Xaa Val Leu Ala Gln
1               5                   10                  15

Leu Ser Ala Arg Xaa Ala Leu Gln Asp Ile Leu Ser Xaa
            20                  25

<210> SEQ ID NO 24
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa at position 2 is D-Ala
<220> FEATURE:
<221> NAME/KEY: misc_feature
<222> LOCATION: (9)..(9)
<223> OTHER INFORMATION: Xaa at position 9 is Cys conjugated to a PEG
      polymer of about 40 kDa
<220> FEATURE:
<221> NAME/KEY: misc_feature
<222> LOCATION: (12)..(12)
<223> OTHER INFORMATION: Xaa at position 12 is L-Ornithine
<220> FEATURE:
<221> NAME/KEY: misc_feature
<222> LOCATION: (21)..(21)
<223> OTHER INFORMATION: Xaa at position 21 is L-Ornithine
<220> FEATURE:
<221> NAME/KEY: misc_feature
<222> LOCATION: (29)..(29)
<223> OTHER INFORMATION: Xaa at position 29 is L-Homoarginine modified
      at the carboxy-terminal with NH2

<400> SEQUENCE: 24

Tyr Xaa Asp Ala Ile Phe Thr Ala Xaa Tyr Arg Xaa Val Leu Ala Gln
1               5                   10                  15

Leu Ser Ala Arg Xaa Ala Leu Gln Asp Ile Leu Ser Xaa
            20                  25

<210> SEQ ID NO 25
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (29)..(29)
<223> OTHER INFORMATION: Xaa at position 29 is Arg modified at the
      carboxy-terminal with NH2

<400> SEQUENCE: 25

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Xaa
            20                  25

<210> SEQ ID NO 26
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(44)
<223> OTHER INFORMATION: Xaa at position 44 is Leu modified at the
      carboxy-terminal with NH2

<400> SEQUENCE: 26

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Xaa
            35                  40

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Gln Gln Gly Glu Ser Asn Gln Glu Arg Gly Ala Arg Ala Arg Leu
1               5                   10                  15
```